US006406718B1

(12) United States Patent
Cooper

(10) Patent No.: US 6,406,718 B1
(45) Date of Patent: Jun. 18, 2002

(54) ORTHORHOMBIC CRYSTALLINE FORM OF FLUTICASONE PROPIONATE AND PHARMACEUTICAL COMPOSITIONS THEREOF

(75) Inventor: Simon Murray Cooper, Ware (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/284,245

(22) PCT Filed: Oct. 23, 1997

(86) PCT No.: PCT/GB97/02929

§ 371 (c)(1),
(2), (4) Date: Apr. 15, 1999

(87) PCT Pub. No.: WO98/17676

PCT Pub. Date: Apr. 30, 1998

(30) Foreign Application Priority Data

Oct. 24, 1996 (GB) .............................................. 9622173

(51) Int. Cl.⁷ ................................................. A61K 9/14
(52) U.S. Cl. ........................ 424/489; 552/632; 552/638; 552/639
(58) Field of Search ................................. 552/632, 638, 552/639; 424/489

(56) References Cited

U.S. PATENT DOCUMENTS

| 4,335,121 | A | * | 6/1982 | Phillips et al. |
| 5,145,684 | A | * | 9/1992 | Liversidge et al. |
| 5,658,549 | A | | 8/1997 | Akehurst et al. |
| 5,674,472 | A | * | 10/1997 | Akehurst et al. |
| 5,795,594 | A | | 8/1998 | York et al. |

FOREIGN PATENT DOCUMENTS

GB          2 088 877          6/1982

OTHER PUBLICATIONS

Phillipps et al., Journal of Medicinal Chemistry, 37(22), 3717–3729 (1994).

* cited by examiner

Primary Examiner—Raj Bawa
(74) Attorney, Agent, or Firm—Bacon & Thomas

(57) ABSTRACT

The invention relates to a new polymorphic crystalline form of S-fluoromethyl 6α,9α-difluoro-11β-hydroxy-16α-methyl-3-oxo-17α-propionyloxyandrosta-1,4-diene-17β-carbothiate (fluticasone propionate). The new polymorphic crystalline form is easily handled and easily fluidised and its particle size and shape can be controlled. The invention also relates to the use of this new material in therapy, particularly in the treatment of respiratory disorders, e.g. asthma.

28 Claims, 24 Drawing Sheets

FIG. 5

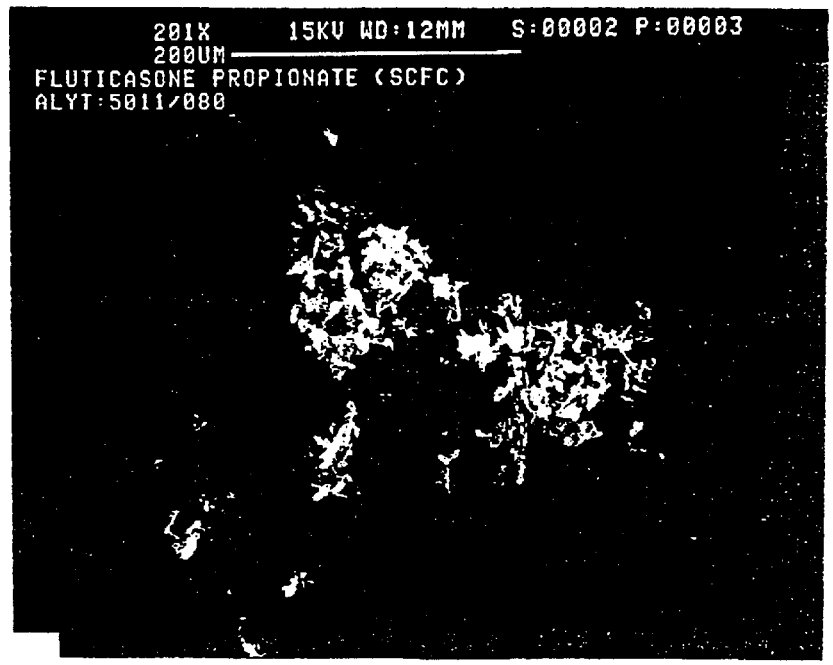
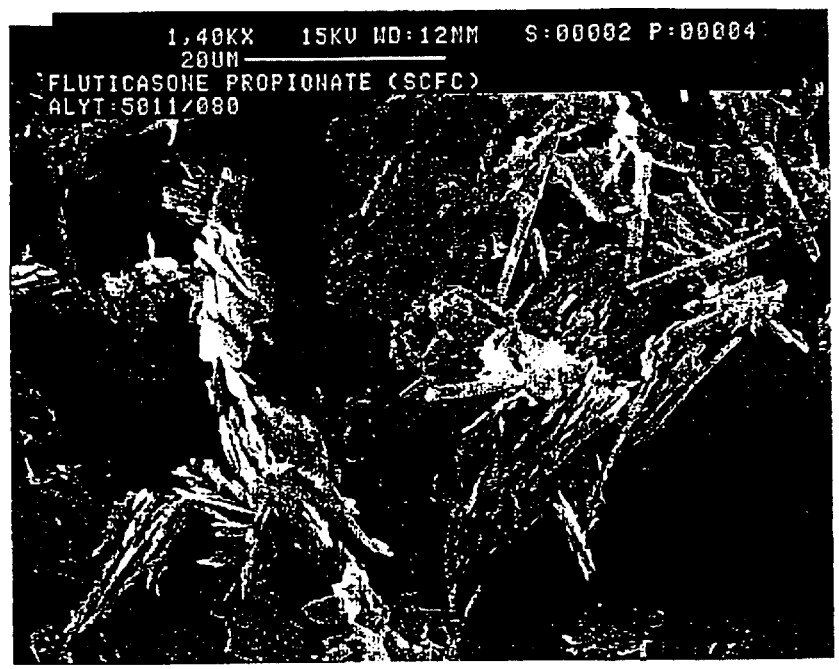
FIG. 6

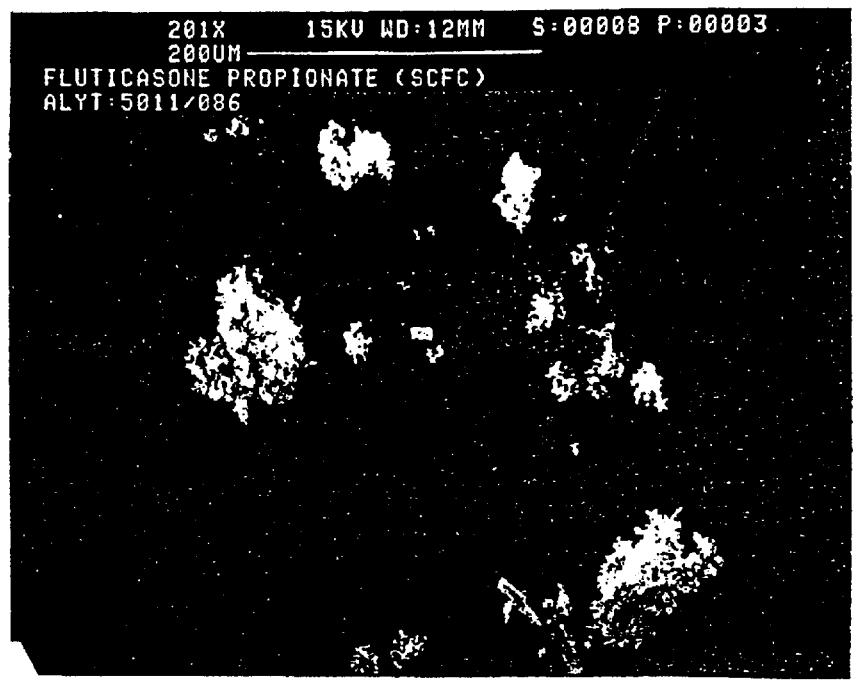
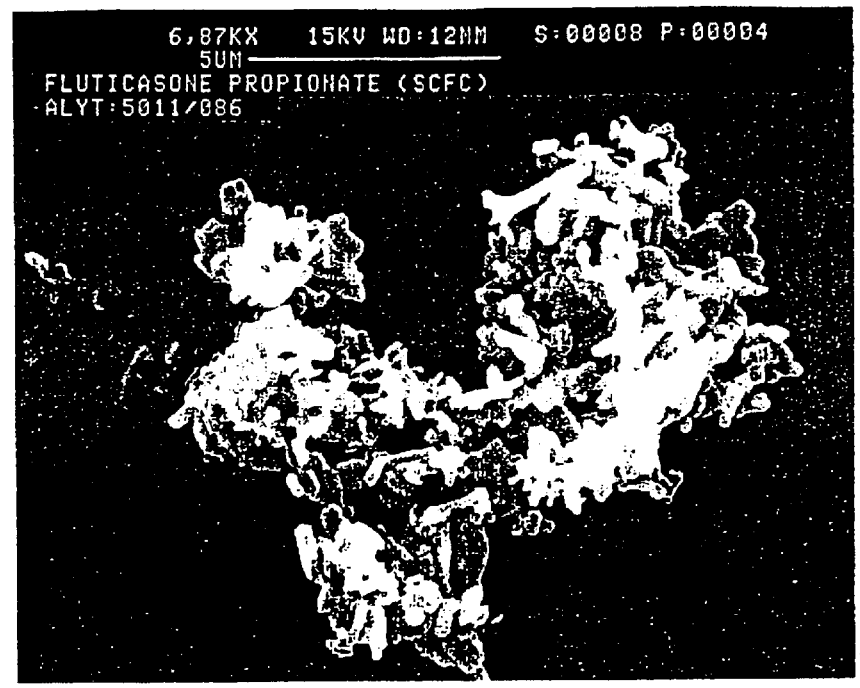
FIG. 7

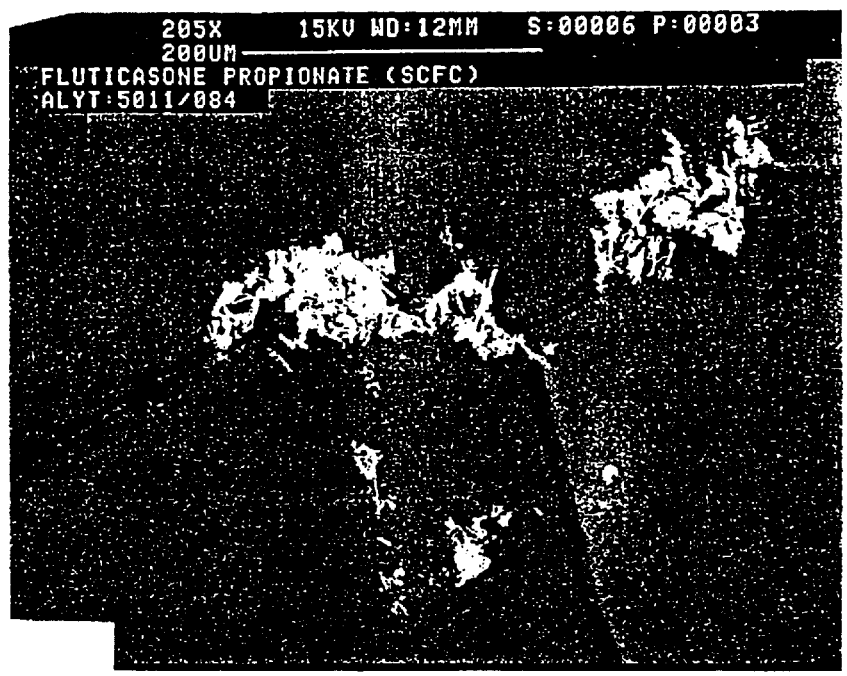
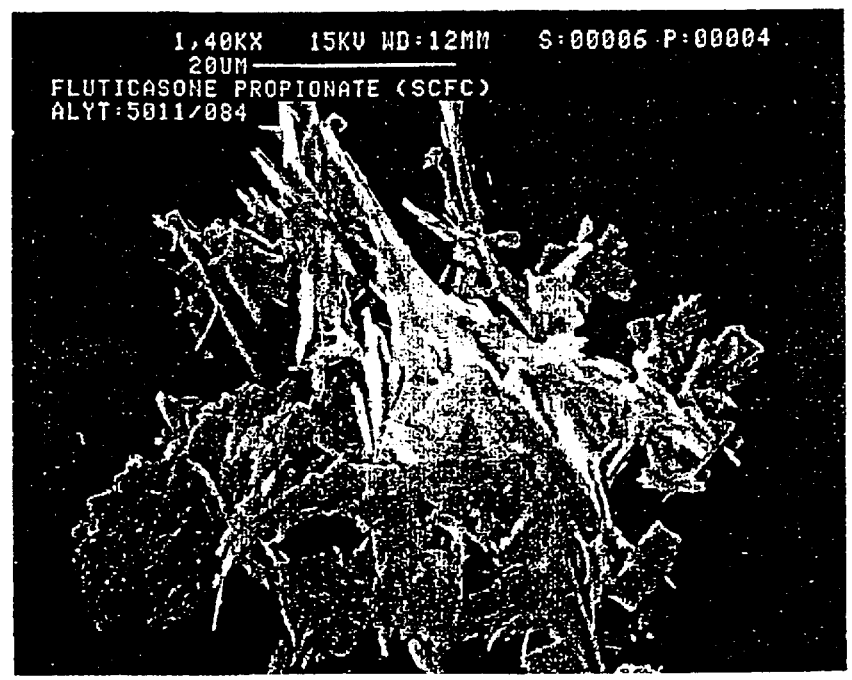
FIG. 8

ORTHORHOMBIC CRYSTALLINE FORM OF FLUTICASONE PROPIONATE AND PHARMACEUTICAL COMPOSITIONS THEREOF

The present invention relates to particulate products which may be prepared by using supercritical fluids. More particularly, the invention relates to novel crystalline forms of fluticasone propionate, which is S-fluoromethyl 6α,9α-difluoro-11β-hydroxy-16α-methyl-3-oxo-17α-propionyloxyandrosta-1,4-diene-17β-carbothiate.

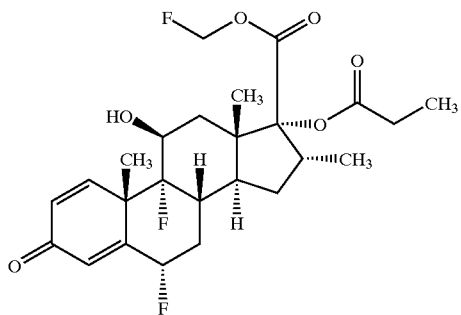

Fluticasone propionate is described and claimed in British Patent No. 2088877 (see Example 14 thereof). This compound has proven anti-inflammatory activity and is particularly useful for the treatment of respiratory disorders, particularly asthma. Fluticasone propionate has been obtained in a crystalline form, designated Form 1, by dissolving the crude product (obtained, e.g. as described in British Patent No. 2088877) in ethyl acetate and then recrystallising. Standard spray-drying techniques have also been shown to lead only to the known Form 1 of fluticasone propionate. According to the present invention, fluticasone propionate may be prepared in a new polymorphic form, designated Form 2. Form 2 may be characterised for example by its X-ray powder diffraction (XRPD) pattern (see infra).

The particulate products of the present invention are produced according to a supercritical fluid technique which we have developed.

The use of supercritical fluids (SCFs) and the properties thereof have been extensively documented, see for instance, J. W. Tom and P. G. Debendetti, "Particle Formation with Supercritical Fluids—A Review", *J. Aerosol. Sci.*, 22 (5), 555–584 (1991). Briefly, a supercritical fluid can be defined as a fluid at or above its critical pressure ($P_c$) and critical temperature ($T_c$) simultaneously. Supercritical fluids have been of considerable interest, not least because of their unique properties. These characteristics include:

High diffusivity, low viscosity and low surface tension compared with liquids.

Large compressibility of supercritical fluids compared with the ideal gas implies large changes in fluid density for slight changes in pressure, which in turn results in highly controllable solvation power. Supercritical fluid densities typically range from 0.1–0.9 g/ml under normal working conditions. Thus, selective extraction with one supercritical fluid is possible.

Many supercritical fluids are normally gases under ambient conditions, which eliminates the evaporation/concentration step needed in conventional liquid extraction.

Most of the commonly used supercritical fluids create non-oxidising or non-degrading atmospheres for sensitive and thermolabile compounds, due to their inertness and moderate temperatures used in routine working conditions. Carbon dioxide is the most extensively used SCF due to its cheapness, non-toxicity, non-flammability and low critical temperature.

These characteristics have led to the development of several techniques of extraction and particle formation utilising supercritical fluids. In particular, two particle formation methods have been identified:

Rapid expansion of supercritical solution (RESS) (see, for instance, J. W. Tom and P. G. Debendetti, supra) involves the dissolution of the solute of interest in a supercritical fluid, followed by rapid expansion of the resulting supercritical solution to atmospheric pressure, resulting in the precipitation of solute particles.

Gas Anti Solvent (GAS) recrystallisation (P. M. Gallagher et al, Supercritical Fluid Science and Technology, ACS Symp. Ser. 406, 134 (1989)) is particularly useful in situations when the solvent of interest does not dissolve in, or has a very low solubility in, a supercritical fluid or a modified supercritical fluid. In this technique, the solute is dissolved in a conventional solvent. A supercritical fluid such as carbon dioxide is introduced into the solution, leading to a rapid expansion of its volume. As a result, the solvent power decreases dramatically over a short period of time, triggering the precipitation of the particles.

There is a need for techniques whereby a product may be obtained with consistent and controlled physical criteria, including control of particle size and shape, quality of the crystalline phase, chemical purity and enhanced handling and fluidising properties.

In addition, it would be advantageous to prepare micronsized particles directly without the need to mill products to this size range. Such milling leads to associated problems such as increased static charge and enhanced particle cohesiveness, as well as reduced yield of product. It also leads to highly stressed particles, which stress may affect the particles, dissolution after administration.

Described in WO95/01324 is an apparatus for the formation of a particulate product in a controlled manner utilising a supercritical fluid particle formation system. The disclosure of WO95/01324 is incorporated herein by this reference. The apparatus comprises a particle formation vessel with means for controlling the temperature of said vessel and means for controlling the pressure of said vessel, together with a means for the co-introduction into said vessel of a supercritical fluid and a vehicle containing at least one substance in solution or suspension, such that dispersion and extraction of the vehicle occur substantially simultaneously by the action of the supercritical fluid.

As used herein, the term "supercritical fluid" means a fluid at or above its critical pressure ($P_c$) and critical temperature ($T_c$) simultaneously. In practice, the pressure of the fluid is likely to be in the range 1.01 $P_c$–7.0 $P_c$, and its temperature in the range 1.01 $T_c$–4.0 $T_c$.

The term "vehicle" means a fluid which dissolves a solid or solids, to form a solution, or which forms a suspension of a solid or solids which do not dissolve or have a low solubility in the fluid. The vehicle can be composed of one or more fluids.

As used herein, the term "supercritical solution" means a supercritical fluid which has extracted and dissolved the vehicle.

The term "dispersion" means the formation of droplets of the vehicle containing at least one substance in solution or suspension.

The term "particulate product" includes products in a single-component or multi-component (e.g. intimate mixtures of one component in a matrix of another) form.

It will be appreciated that, where necessary, the apparatus may additionally comprise a means for the collection of the particulate product, for example, a means for the retention of the product in the particle formation vessel, such as a filter, thus reducing loss of the product together with the resultant supercritical solution. An alternative means may involve a cyclone separating device.

The apparatus mentioned above and its use provide the opportunity for manufacturing dry particulate products with controlled particle size and shape by offering control over the working conditions, especially the pressure, utilising, for example, an automated back-pressure regulator such as model number 880-81 produced by Jasco Inc. Such an improved control eliminates pressure fluctuation across the particle formation vessel and ensures a more uniform dispersion of the vehicle (containing at least one substance in solution or suspension) by the supercritical fluid with narrow droplet size distribution during the particle formation process. There is little or no chance that the dispersed droplets will reunite to form larger droplets since the dispersion occurs by the action of the supercritical fluid which also ensures thorough mixing with the vehicle and rapidly removes the vehicle from the substance(s) of interest, leading to particle formation.

The simultaneous co-introduction of the vehicle containing at least one substance in solution or suspension and the supercritical fluid, according to the method described herein, allows a high degree of control of parameters such as temperature, pressure and flow rate, of both vehicle fluid and supercritical fluid, at the exact point when they come into contact with one another.

Further advantages for particles formed as described herein include control over the quality of the crystalline and polymorphic phases, since the particles will experience the same stable conditions of temperature and pressure when formed, as well as the potential of enhanced purity. This latter feature can be attributed to the high selectivity of supercritical fluids under different working conditions, enabling the extraction of one or more of the impurities from the vehicle containing the substance of interest.

The means for the co-introduction of the supercritical fluid and the vehicle into the particle formation vessel preferably allows for them to be introduced with concurrent directions of flow, and more preferably takes the form of a coaxial nozzle as described below. This ensures no contact between the formed particles and the vehicle fluid around the nozzle tip area. Such contact would reduce control of the final product size and shape. Extra control over the droplet size, in addition to that provided by nozzle design, is achieved by controlling the flow rates of the supercritical fluid and the vehicle fluid. At the same time, retaining the particles in the particles formation vessel eliminates the potential of contact with the vehicle fluid that might otherwise take place on depressurising the supercritical solution. Such contact would affect the shape and size, and potentially the yield, of the product.

Thus, in the apparatus described herein and in WO95/01324 the means for the co-introduction of the supercritical fluid and the vehicle (containing at least one substance in solution or suspension) into the particle formation vessel preferably comprises a nozzle the outlet end of which communicates with the interior of the vessel, the nozzle having coaxial passages which terminate adjacent to one another at the outlet end, at least one of the passages serving to carry a flow of the supercritical fluid, and at least one of the passages serving to carry a flow of the vehicle in which a substance is dissolved or suspended.

Preferably, the opening at the outlet end (tip) of the nozzle will have a diameter in the range of 0.05 to 2 mm, more preferably between 0.1 and 0.3 mm, typically about 0.2 mm. The angle of taper of the outlet end will depend on the desired velocity of the fluids introduced through the nozzle; an increase in the angle may be used, for instance, to increase the velocity of the supercritical fluid introduced through the nozzle and hence to increase the amount of physical contact between the supercritical fluid and the vehicle. Typically (although not necessarily) the angle of taper will be in the range of about 10° to about 50°, preferably between about 20° and about 40°, more preferably about 30°. The nozzle may be made of any appropriate material, for example stainless steel.

In one embodiment, the nozzle has two coaxial passages, an inner and an outer. In another, preferred, embodiment, the nozzle has three coaxial passages, an inner, an intermediate and an outer. This latter design allows greater versatility in use of the apparatus, since if necessary two vehicles may be introduced into the particle formation vessel with the supercritical fluid. Improved dispersion and finer particles can also be obtained if such a nozzle is used to introduce a flow of the vehicle sandwiched between an inner and an outer flow of the supercritical fluid, since this ensures that both sides of the vehicle are exposed to the supercritical fluid. It is, however, to be appreciated that the nozzle may have any appropriate number of coaxial passages.

The internal diameters of the coaxial passages may be chosen as appropriate for any particular use of the apparatus. Typically, the ratio of the internal diameters of the outer and the inner passages may be in the range of from 2 to 5, preferably between about 3 and 5. Where an intermediate passage is included, the ratio of the internal diameters of the outer and intermediate passages may be in the range of from 1 to 3, preferably between about 1.4 and 1.8.

Particular examples of such coaxial nozzles and their typical dimensions are illustrated in FIGS. 2A, 2B and 4 herein.

The temperature of the particle formation vessel may be maintained (preferably ±0.1° C.) by means of a heating jacket or, more preferably, an oven. The pressure of the particle formation vessel is conveniently maintained (preferably ±2 bar) by means of a back-pressure regulator. It will be appreciated that such apparatus will be readily available from, for example, manufacturers of supercritical fluid extraction equipment, for instance, from Jasco Inc., Japan.

The invention provides a method for the formation of a particulate fluticasone propionate product which comprises the co-introduction of a supercritical fluid and a vehicle containing at least fluticasone propionate in solution or suspension into a particle formation vessel, the temperature and pressure in which are controlled, such that dispersion and extraction of the vehicle occur substantially simultaneously by the action of the supercritical fluid.

Dispersion and extraction will also typically occur substantially immediately on introduction of the fluids into the particle formation vessel. Co-introduction of the supercritical fluid and the vehicle containing at least fluticasone propionate in solution or suspension preferably is effected using a nozzle of coaxial design.

Suitably the particle formation vessel used is as described in WO95/01324.

Suitable chemicals for use as supercritical fluids include carbon dioxide, nitrous oxide, sulphur hexafluoride, xenon, ethylene, chlorotrifluoromethane, ethane and trifluoromethane. Particularly preferred is carbon dioxide.

The supercritical fluid may optionally contain one or more modifiers, for example, but not limited to, methanol, ethanol, ethyl acetate, acetone, acetonitrile or any mixture thereof. When used, the modifier preferably constitutes not more than 20%, and more particularly constitutes between 1 and 10%, of the supercritical fluid.

The term "modifier" is well known to those persons skilled in the art. A modifier (or co-solvent) may be described as a chemical which, when added to a supercritical fluid, changes the intrinsic properties of the supercritical fluid in or around the critical point.

Regarding the choice of vehicle for the fluticasone propionate, where the fluticasone propionate is to be handled as a solution it should be soluble in the chosen vehicle, and the chosen vehicle should be soluble in the chosen supercritical fluid. The choice of a suitable combination of supercritical fluid, modifier (where desired) and vehicle for any desired product will be well within the capabilities of a person of ordinary skill in the art.

Suitable solvents may be, for example, methanol, ethanol, ethyl acetate, acetone, acetonitrile or any mixture thereof.

Control of parameters such as size, shape and crystal habit in the particulate product will be dependent upon the operating conditions used when carrying out the method of the invention. Variables include the flow rates of the supercritical fluid and/or the vehicle containing substance(s), the vehicle used to dissolve the substance(s), the concentration of the substance(s) in the vehicle, and the temperature and pressure inside the particle formation vessel.

It will also be appreciated that the precise conditions of operation of the present apparatus will be dependent upon the choice of supercritical fluid and whether or not modifiers are present.

Table 1 lists the critical pressure and temperatures for some selected fluids:

TABLE 1

| Fluid | $P_c$ (bar) | $T_c$ (° C.) |
|---|---|---|
| carbon dioxide | 74 | 31 |
| nitrous oxide | 72 | 36 |
| sulphur hexafluoride | 37 | 45 |
| xenon | 58 | 16 |
| ethylene | 51 | 10 |
| chlorotrifluoromethane | 39 | 29 |
| ethane | 48 | 32 |
| trifluoromethane | 47 | 26 |

In practice, it may be preferable to maintain the pressure inside the particle formation vessel substantially in excess of the $P_c$ (for instance, 100–300 bar for carbon dioxide) whilst the temperature is above the $T_c$ (e.g. 35–75° C. for carbon dioxide).

The flow rates of the supercritical fluid and/or the vehicle may also be controlled so as to achieve a desired particle size, shape and/or form. Although the flow ratio will be dependent on the desired characteristics of the fluticasone propionate, typically the ratio of the vehicle flow rate to the supercritical fluid flow rate will be between 0.001 and 0.1, preferably between 0.01 and 0.07, more preferably around 0.03.

The method described herein preferably additionally involves collecting the particulate product following its formation. It may also involve recovering the supercritical solution formed, separating the components of the solution and recycling one or more of those components for future use.

According to a preferred aspect of the present invention, there is provided the compound fluticasone propionate in an easily handled and easily fluidised crystalline form, with a controlled particle size and shape, and optionally also with a controlled morphology and level of agglomeration.

The invention also provides a new crystalline form of fluticasone propionate, designated Form 2 fluticasone propionate as described herein. The precise conditions under which Form 2 fluticasone propionate is formed may be empirically determined; herein (see Example 5) we give a number of examples of methods which have been found to be suitable in practice.

As mentioned above, control of parameters such as size, shape and crystal habit in the particulate product will be dependent upon the operating conditions used when carrying out the method of the invention. By appropriate adjustment of the variables of the process, the relative amounts of Forms 1 and 2 of fluticasone propionate produced with the apparatus described herein may be altered by the person skilled in the art. The experimental domains for each polymorphic form can be determined empirically for the particular apparatus employed.

Conventionally crystallised fluticasone propionate, even after micronisation (fluid milling), exists in a form with very poor flow characteristics, for example it is cohesive and statically charged, which results in difficulties in handling the drug substance in pharmaceutical formulation processes.

In another aspect of the present invention, there is provided fluticasone propionate in a form with a dynamic bulk density of less than 0.2 g $cm^{-3}$. In a preferred aspect of the present invention, there is provided fluticasone propionate in a form with a dynamic bulk density in the range between 0.05 and 0.17 g $cm^{-3}$, and, in particular, in the range between 0.05 and 0.08 g $cm^{-3}$.

The dynamic bulk density (W) is indicative of a substance's fluidisability and is defined as:

$$W = \frac{(P - A)C}{100} + A$$

where P is the packed bulk density (g $cm^{-3}$), A is the aerated bulk density (g $cm^{-3}$) and C is the compressibility (%) where C is calculated by the equation:

$$C = \frac{P - A}{P} \times 10$$

Clearly, a low figure for W corresponds to a high degree of fluidisability.

When compared against conventionally crystallised fluticasone propionate, both before and after micronisation, fluticasone propionate of the present invention exhibits a significantly lower dynamic bulk density than the conventionally crystallised fluticasone propionate as illustrated in Table 7 (see Example 6 below).

It will be appreciated that in the case of an inhaled pharmaceutical, such as fluticasone propionate, it is particularly desirable to produce a drug substance which is readily fluidisable, thereby potentially improving its inhalation properties.

The fluticasone propionate of the present invention is observed to have improved handling and fluidising characteristics compared with conventionally crystallised fluticasone propionate.

Furthermore, the particle size and shape of provided fluticasone propionate of the present invention can be controlled as illustrated by the electronmicrographs herein.

Preferably, the fluticasone propionate of the present invention is within the particle size range suitable for pharmaceutical dosage forms to be delivered by inhalation or insufflation. A suitable particle size range for this use is 1 to 10 microns, preferably 1 to 5 microns. Particles generally have a uniform particle size distribution, as measured by a uniformity coefficient of from 1 to 100, typically 1 to 20 e.g. 5 to 20.

The particle size distribution of the fluticasone propionate according to the invention may be measured by conventional techniques, for example by laser diffraction, by the "Twin Impinger" analytical process or by the "Cascade Impaction" analytical process. As used herein reference to the "Twin Impinger" assay means "Preparations for Inhalation: Aerodynamic assessment of fine particles using apparatus A" as defined in the British Pharmacopoeia 1993, Addendum 1996, pages A522–527 as applied to a dry powder inhalation formulation. As used herein reference to the "Cascade Impaction" assay means "Preparations for Inhalation: Aerodynamic assessment of fine particles using apparatus D" as defined in the British Pharmacopoeia 1993, Addendum 1996, page 527 as applied to a metered dose inhaler formulation. The preferred fluticasone propionate according to the invention of mean particle size between 1 and 10 microns has been found to have a respirable fraction of 14% or more by weight.

The fluticasone propionate of the present invention typically has a low cohesivity, for example of 0 to 20%, preferably 0 to 10% employing methods of measurement based on those described by R. L. Carr in Chemical Engineering 1965, 163–168.

The fluticasone propionate according to the invention may be used to prepare a pharmaceutical composition which may be presented for use in a conventional manner with the aid of a pharmaceutically acceptable carrier or excipient, optionally with supplementary medicinal agents. Preferred carriers include, for example, polymers e.g. starch and hydroxypropylcellulose, silicon dioxide, sorbitol, mannitol and lactose e.g. lactose monohydrate. The compositions may be in a form suitable for administration by inhalation or insufflation, or for oral, buccal, parenteral, topical (including nasal) or rectal administration. Administration by inhalation or insufflation is preferred.

In a preferred pharmaceutical composition according to the invention the fluticasone propionate and carrier are co-crystallised together using the process and apparatus described herein to form multicomponent particles comprising both fluticasone propionate and carrier. Such multicomponent particles represent a further aspect of the invention.

In a preferred aspect the invention provides a pharmaceutical composition in the form of a dry powder suitable for inhalation or insufflation which comprises fluticasone propionate according to the present invention and a suitable powder base such as lactose or starch, preferably lactose, as carrier. Especially preferred are compositions comprising fluticasone propionate and lactose in the form of multicomponent particles. The dry powder composition may be presented in unit dosage form in, for example, capsules or cartridges of e.g. gelatin, or blister packs from which the powder may be administered with the aid of an inhaler or insufflator.

For administration by inhalation the fluticasone propionate made in accordance with the invention may be conveniently delivered in the form of an aerosol spray presentation from pressurised packs such as metered dose inhalers, with the use of a suitable propellant, such as dichlorodifluoromethane or preferably a fluorocarbon or hydrogen-containing fluorocarbon such as HFA134a (1,1,1,2-tetrafluoroethane), HFA227 (1,1,1,2,3,3,3-heptafluoro-n-propane) or mixtures thereof. Such aerosol spray presentations may include surfactants, e.g. oleic acid or lecithin; co-solvents, e.g. ethanol; or other excipients conventionally used in such formulations.

The formulations for administration by inhalation or insufflation are intended for administration on a prophylactic basis to humans suffering from allergic and/or inflammatory conditions of the nose, throat or lungs such as asthma and rhinitis, including hay fever. Aerosol formulations are made so that each metered dose or "puff" of aerosol contains from 20 to 1000 micrograms, preferably 25 to 150 micrograms of fluticasone propionate of the invention. Administration may be several times daily, for example 2, 3, 4 or 8 times, giving for example 1, 2 or 3 doses each time. The overall daily dose with an aerosol will be within the range 100 micrograms to 10 mg, preferably 100 micrograms to 1.5 mg.

There follows a brief description of the Figures:

FIGS. 5 to 7 are scanning electron microscopy (SEM) photographs of fluticasone propionate, as prepared in Example 2.

FIG. 8 is an (SEM) photograph of fluticasone propionate, as prepared in Example 3.

Figure 1:
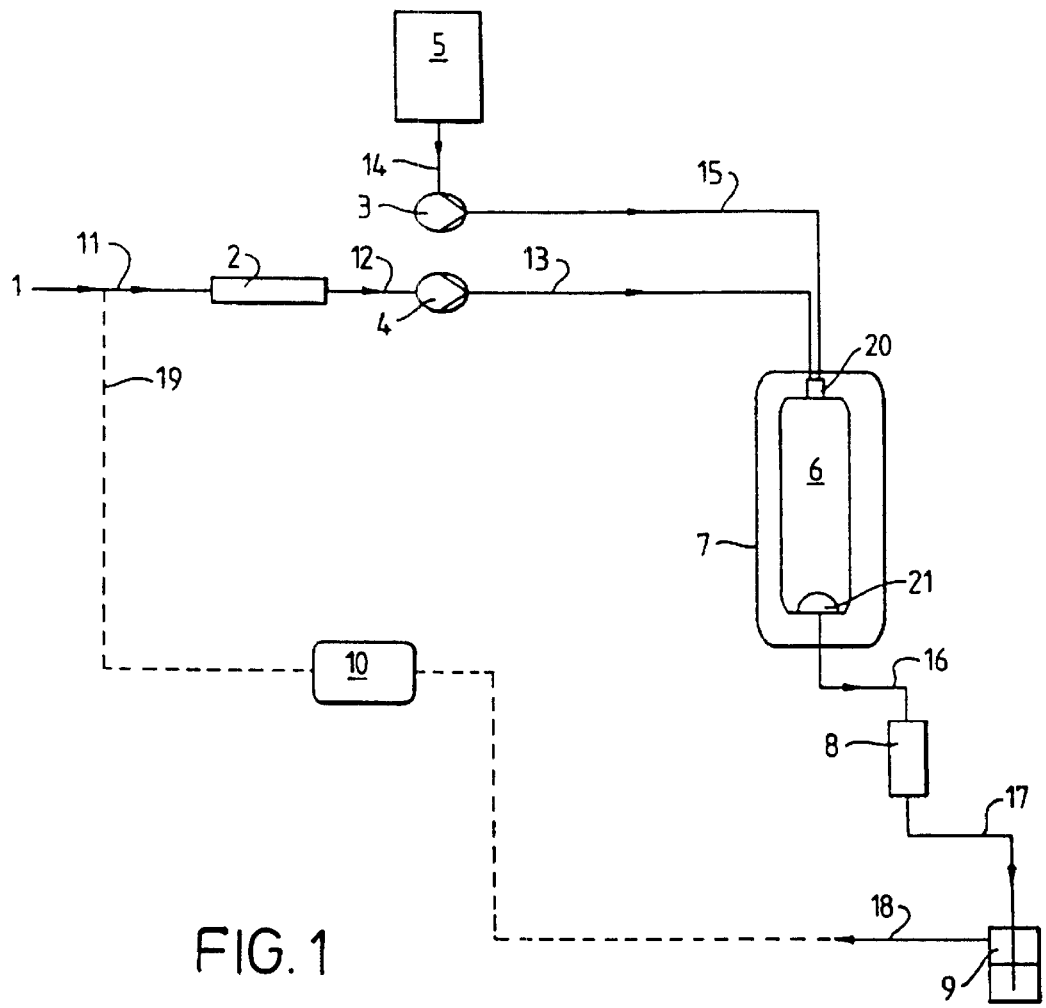
FIG. 1 shows a schematic design of an apparatus described herein.
Figure 2A:
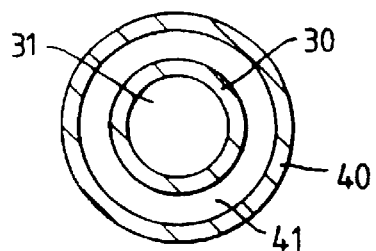
FIG. 2A shows a cross-section of a coaxial nozzle for use in the apparatus described herein.
Figure 2B:
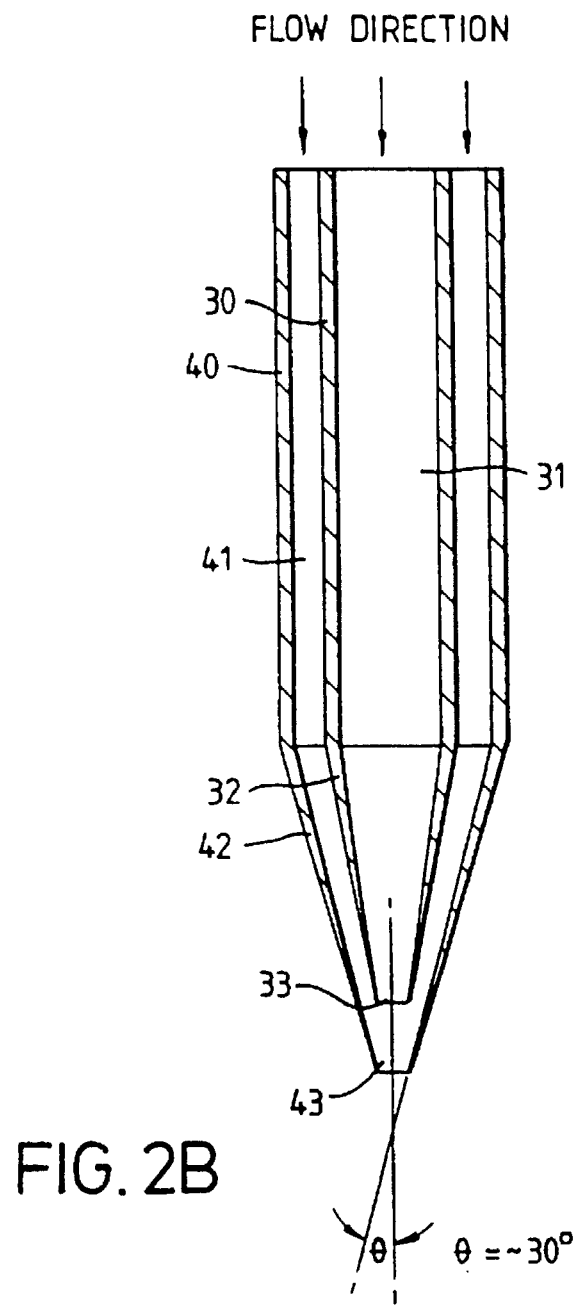
FIG. 2B shows a longitudinal section of a tip of a coaxial nozzle for use in the apparatus described herein.
Figure 3A:
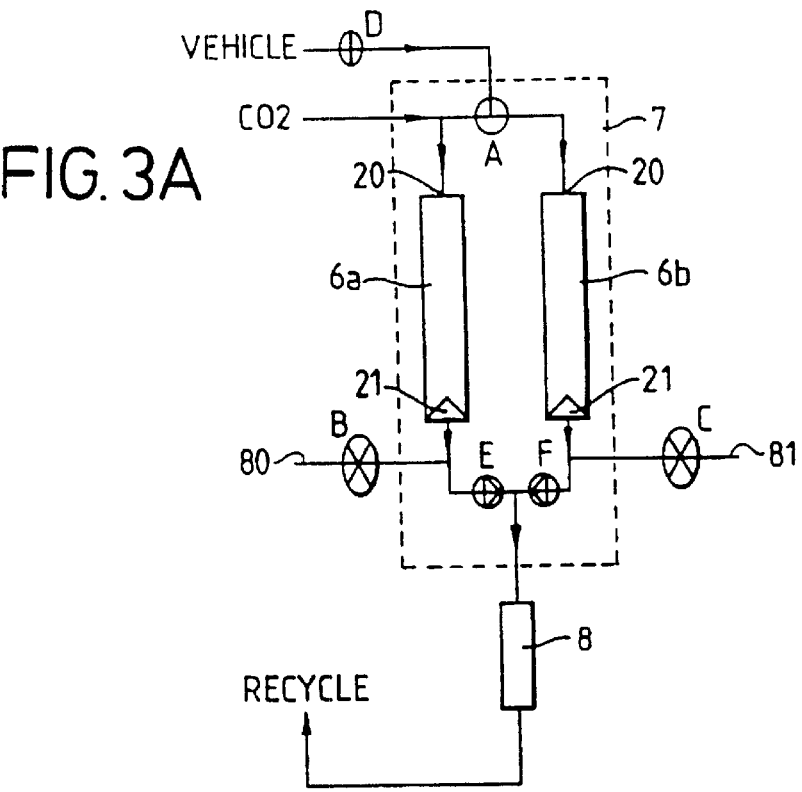
FIGS. 3A and 3B show schematic designs of alternative apparatuses.
Figure 3B:
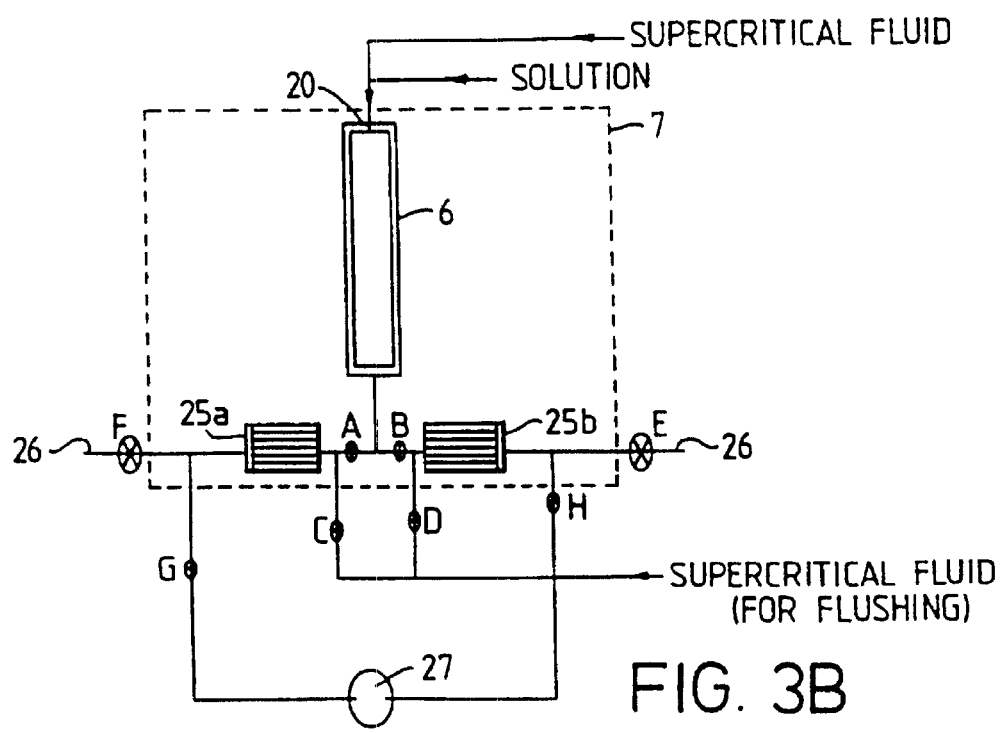
Figure 4:
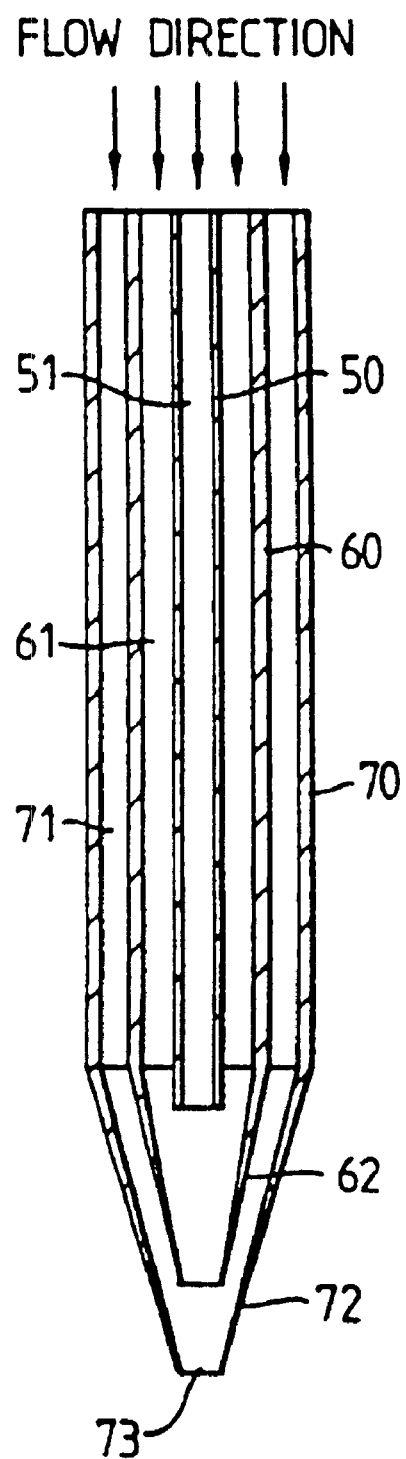
FIG. 4 shows a longitudinal section of the tip of an alternative coaxial nozzle.

There follows a detailed description of a preferred embodiment of the apparatus and method described herein with reference to FIGS. 1, 2, 3 and 4. FIGS. 1 and 3 are simplified diagrammatic flow sheets of apparatus and FIGS. 2A, 2B and 4 show nozzles which may be used therein.

Referring to FIG. 1, the apparatus includes a particle formation vessel 6. This is typically a standard reaction vessel, for instance of the type available from Keystone Scientific Inc., of an appropriate capacity for the particular use to which it is to be put. The temperature and pressure of the vessel are maintained at constant desired level, by means of an oven 7 and back-pressure regulator 8, respectively.

In use, the system is initially pressurised and stable working conditions are met. A suitable gas, for example, carbon dioxide, is fed from source 1 via conduit 11 to a cooler 2, to ensure liquification, and is fed by conduit 12 to a pump 4. From there it is fed by conduit 13 to the vessel 6 via a nozzle 20. A solution or dispersion of a solid of interest, in this case fluticasone propionate, in a suitable vehicle, for example methanol, is drawn from source 5 by a conduit 14 to a pump 3 and is fed by conduit 15 to the vessel 6 via a nozzle 20.

The nozzle 20 may be as shown in either FIG. 2 (A and B) or FIG. 4. That shown in FIG. 2 comprises coaxial inner and outer tubes 30 and 40, respectively. These define an inner passage 31 and an outer passage 41. The tubes 30 and 40 have conically tapering end portions 32 and 42, respectively. The tips of the end portions 32 and 42 define respective orifices 33 and 43, with the orifice 43 being a short distance downstream of the orifice 33. As indicated in FIG. 2B, the angle of taper of the end portion 42 is about 30° in this (non-limiting) example.

The alternative nozzle illustrated in FIG. 4 comprises three coaxial tubes 50, 60 and 70 which define an inner passage 51, an intermediate passage 61, and an outer passage 71 respectively. Tubes 60 and 70 have conically tapering end portions 62 and 72, the angle of taper of the end portion 72 being about 30° in this example.

The nozzle of FIG. 4 allows three fluids to be introduced into the vessel 6 at the same time, leading to greater versatility in use of the apparatus. For instance, it is possible to add through one of the three passages a desired carrier or other additive intended to form part of, or be mixed with, the final particulate product. The additive is then dispersed simultaneously with the substance of primary interest. Also, in situ reactions may be carried out immediately prior to dispersion by the supercritical fluid, by introducing two or more reactants in two separate vehicles through two of the nozzle passages, the reaction occurring at the passage outlets either immediately prior to, or on, dispersion.

Alternatively, the nozzle of FIG. 4 may be used to introduce a flow of the vehicle (passage 61) sandwiched between an inner and an outer flow of the supercritical fluid (passages 51 and 71). This leads to improved dispersion of the vehicle, and hence to greater control over, and uniformity of, particle size in the final product; indeed it makes possible the formation of finer products than may be achieved using a two-passage nozzle.

In the nozzle shown, inner tube 50 has an internal diameter of 0.25 mm; intermediate tube 60 has an internal diameter of 0.53 mm; and outer tube 70 has an internal diameter of 0.8 mm and an outside diameter of 1.5 mm. The tip opening (73) has an internal diameter of 0.2 mm. The tubes are all made of stainless steel.

However, the nozzle may be made of any appropriate material and have any suitable dimensions. For instance, the internal diameters may be in the ranges 0.05–0.35 mm (inner); 0.25–0.65 mm (intermediate); and 0.65–0.95 mm (outer), preferably between 0.1 and 0.3 mm (inner); 0.3 and 0.6 mm (intermediate); and 0.07 and 0.9 mm (outer). The tip opening is likely to have an internal diameter in the range of 0.1–0.3 mm, preferably between 0.18 and 0.25 mm.

In the apparatus of FIG. 1, the supercritical fluid is fed under pressure (at high flow rate when compared with the flow rate of the vehicle) through for example the inner nozzle passage 31 of the nozzle shown in FIG. 2, and the solution or suspension of the solid of interest in a vehicle (hereinafter referred to as the "liquid") is simultaneously fed under pressure through the outer passage 41. It is believed that the high velocity supercritical fluid emerging from the orifice 33 causes the liquid emerging from the end of outer passage 41 to be broken up into droplets from which the vehicle is substantially simultaneously extracted by the supercritical fluid to result in the formation of particles of the solid previously held in the vehicle. It is to be understood, however, that although it is believed that this is what occurs, we do not wish to be bound by this theoretical explanation, and the actual physical processes occurring may not be precisely as just indicated.

Also, although the configuration has been described in which the supercritical fluid passes through the inner passage 31 and the vehicle passes through the outer passage 41, the configuration may be reversed, with the supercritical fluid in the outer passage 41 and the vehicle in the inner passage 31. Similarly in the nozzle of FIG. 4, any one of the three passages may be used to carry any one of a number of desired fluids, as appropriate.

The nozzle 20 ensures dispersion of the vehicle containing the solid of interest, the shearing action of the high velocity supercritical fluid and also thorough mixing of the dispersed vehicle with the supercritical fluid which simultaneously extracts the vehicle from the dispersed liquid, resulting in substantially immediate particle formation of the solid of interest. Because the supercritical fluid and vehicle are introduced coaxially, and dispersion occurs substantially simultaneously with vehicle extraction, a very high degree of control is possible of the conditions (e.g. pressure, temperature and flow rate) affecting particle formation, at the exact time when it occurs.

The particles formed are retained in the particle formation vessel by collecting means 21. The resultant supercritical solution is fed by conduit 16 to a back-pressure regulator 8 and is then fed by conduit 17 to a separation vessel 9 where it expands to cause the supercritical fluid to separate as a gas from the liquid vehicle. The gas may be fed by conduit 18 to a tank 10 and returned by conduit 19 to the cooler 2. The vehicle may also be collected for subsequent use. Means, not shown, may be provided to smooth the flow pulse of fluids and vehicles produced by pumps 3 and 4, so as to eliminate, or at least reduce, any flow pulsations.

When sufficient particle formation has occurred in the vessel 6, it is flushed through with clean, dry supercritical fluid, so as to ensure removal of any residual vehicle. The vessel can then be depressurised and particulate product removed.

The alternative apparatuses shown schematically in FIGS. 3A and 3B are for use in continuous particle formation. That shown in FIG. 3A includes two particle formation vessels 6*a* and 6*b*, each of the type shown in FIG. 1 and each including an inlet nozzle 20 and a particle collecting means (such as a filter) 21. Oven 7 serves both vessels.

In the apparatus in FIG. 3A, valve A controls the supply of the supercritical fluid and the vehicle (containing the substance of interest) to the two vessels 6*a* and 6*b*, and one-way valves E and F control the outlets from the two vessels to the back-pressure regulator 8. Valve D controls the supply of the vehicle to valve A. Valves B and C are needle valves, and items 80 and 81 are vents.

The apparatus may be "continuously" operated as follows. Valve A is firstly set to supply fluids to vessel 6*a*, in which particle formation is allowed to occur, as described in connection with FIG. 1. Valve E is set so that the resultant supercritical solution may drain from vessel 6*a* to the back-pressure regulator 8 for subsequent recycling.

When sufficient particle formation has occurred, valve D is closed to stop the flow of vehicle, whilst the supercritical fluid continues to flow through vessel 6*a* to dry (flush) the products. Valve A is then set to supply fluids to the empty vessel 6*b* and valve D re-opened, whilst valve B is opened so as slowly to depressurise vessel 6*a*. One-way valve E eliminates any chance of a back-flow from vessel 6*b* or of disruption of the particle formation process now occurring in vessel 6*b*. Vessel 6*a* is removed for collection of the product, and then refitted and repressurised ready for re-use. Supercritical solution drains from vessel 6b via valve F, which is set appropriately.

Once particle formation in vessel 6b is complete, the valves are set back to allow it to continue in vessel 6a, whilst 6b is flushed and emptied. In this way, particle formation in the apparatus can continue uninterrupted.

The apparatus shown in FIG. 3B includes only one particle formation vessel 6, which does not contain any particle collecting means, and two particle collection vessels 25a and 25b downstream of vessel 6. The supercritical fluid carries the formed particles to the collection vessels 25a and 25b.

The apparatus also includes an inlet nozzle 20, two vents 26, a back pressure regulator 27, an oven 7 and valves A–H. Supercritical fluid and solution (vehicle) are fed to the nozzle 20 where shown.

The apparatus might be used as follows. Initially, (valves C, D, E, and F closed) the system is pressurised and stable working conditions are met; valves B and H are then closed, driving the flow of supercritical fluid through valve A only. The vehicle and substance of interest are introduced into vessel 6 and the particles formed are transported by the supercritical fluid via valve A to collection vessel 25a which contains a particle retention device. The retention device is placed at the outlet of the vessel to ensure maximum collection volume. The solid-free supercritical solution (the supercritical fluid and the vehicle) flows across valve G to the back pressure regulator 27. On emerging from the back pressure regulator the supercritical solution expands into a large pressure resistant vessel (not shown), where the vehicle separates from the gas and both can be recycled.

When the collection vessel 25a is full, switching takes place, closing valves A and G and simultaneously opening valves B and H. This allows the flow of the supercritical solution, emerging from vessel 6, into the second collection vessel 25b. Valves C and G are opened after flow switching to ensure a high flow of supercritical fluid to flush the full collection vessel 25a, i.e. the supercritical solution volume is replaced by a supercritical fluid volume. It is estimated that 1–2 times the volume of the collection vessel, of the supercritical fluid, ensures a dry powder. The flushing time is generally short owing to the fact that the particles are occupying the volume of the collection vessel. After flushing, valves C and G are closed and valve F (a needle valve) is slowly opened to the full collection vessel 25a. Since the particulate product takes up the vessel volume only a small amount of supercritical fluid is discharged, mainly the internal volume of the fittings involved.

The full collection vessel 25a is removed and the dry powder collected. After refitting and repressurising via valve C, the vessel is ready for re-use as soon is the second collection vessel 25b, which has meantime been collecting product from vessel 6, is full.

The benefits of using the apparatus of FIG. 3B include:

1. The elimination of depressurising and pressurising steps of the reaction vessel every time product is collected. This could mean considerable reductions in the amounts of fluids being discharged, in particular when using a large volume particle formation vessel (scaling up) or expensive high purity gases.

2. Significant time saving during the flushing (drying) procedure. In a batch particle formation process only a rather small volume of the reaction vessel is occupied by the product and the remaining volume (where dispersion takes place) is taken up by the supercritical solution. This mixture will eventually be replaced by at least the same volume of the supercritical fluid in the flushing procedure, which can therefore take a long time when scaled up.

3. The environment and workers are less exposed to the products during the recovery step. In some cases it is difficult to collect products directly from a large reaction vessel due to handling inconvenience or because the products of interest are sensitive to light, oxygen or humidity, which might affect their characteristics or purity.

The invention is further illustrated by the following non-limiting examples. Examples 1 to 9, illustrating the preparation of fluticasone propionate and its physical properties, were carried out using apparatus of the type illustrated in FIGS. 1 and 2, using a 32 ml particle formation vessel and a two-passage coaxial nozzle having the following dimensions:

|  | outer diameter | inner diameter |
|---|---|---|
| outer tube: | 1.58 mm | 0.75 mm |
| inner tube: | 0.63 mm | 0.20 mm |

The tip orifice (43 in FIG. 2B) was 0.32 mm in diameter, and both the inner and outer tubes were made of stainless steel.

EXAMPLE 1

Particle Size Distribution

The data for four samples of fluticasone propionate of the present invention, produced using the method and apparatus described herein, are presented in Table 2 below. The particle size was determined by laser diffraction (Malvern Mastersizer).

Sample 1 was produced using a solution of fluticasone propionate in acetone (2.5% w/v) which was co-introduced with $CO_2$ at 300 bar, 35° C. and a flow rate ratio of 0.014 via a coaxial nozzle into the particle formation vessel.

Sample 2 was produced using a solution of fluticasone propionate in acetone (0.5% w/v) which was co-introduced with $CO_2$ at 100 bar, 35° C. and a flow rate ratio of 0.014 via a coaxial nozzle into the particle formation vessel.

Sample 3 was produced using a solution of fluticasone propionate in ethyl acetate (0.5% w/v) which was co-introduced with $CO_2$ at 100 bar, 75° C. and a flow rate ratio of 0.043 via a coaxial nozzle into the particle formation vessel.

Sample 4 was produced using a solution of fluticasone propionate in acetone (2.5% w/v) which was co-introduced with $CO_2$ at 100 bar, 75° C. and a flow rate ratio of 0.014 via a 3-component coaxial nozzle into the particle formation vessel.

The data presented in Table 2 show that the particle size can be manipulated depending on the conditions. The particle size data for sample 4 indicate that a particle size similar to that of conventionally crystallised fluticasone propionate (micronised) can be achieved. The uniformity index is not significantly different from that of the conventionally crystallised fluticasone propionate (micronised).

TABLE 2

|  | Mean particle size ($\mu$m) | % <5 $\mu$m | % <10 $\mu$m | Uniformity Index |
|---|---|---|---|---|
| Conventionally crystallised | 1–3 | Typically >90 | Typically >95 | 15 |

TABLE 2-continued

| | Mean particle size (μm) | % <5 μm | % <10 μm | Uniformity Index |
|---|---|---|---|---|
| fluticasone propionate (micronised) | | | | |
| Sample 1 | 5.2 | 48 | 81 | 12 |
| Sample 2 | 10.4 | 20 | 48 | 13 |
| Sample 3 | 31.0 | 6 | 13 | 12 |
| Sample 4 | 2.8 | 68 | 83 | 4 |

EXAMPLE 2

Particle Shape Data

The particle shape was determined by scanning electron microscopy. Data for three samples of fluticasone propionate of the present invention, produced using the method and apparatus described herein, are presented in FIGS. 5 to 7.

Sample 5 was produced using a solution of fluticasone propionate in methanol (0.5% w/v) which was co-introduced with $CO_2$ at 100 bar, 75° C. and a flow rate ratio of 0.043 via a coaxial nozzle into the particle formation vessel. The particle shape is described as acicular with a high aspect ratio up to 200:1 (FIG. 5).

Sample 6 was produced using a solution of fluticasone propionate in acetone (1.5% w/v) which was co-introduced with $CO_2$ at 200 bar, 55° C. and a flow rate ratio of 0.029 via a coaxial nozzle into the particle formation vessel. The particle shape is described as flake-like (FIG. 6).

Sample 7 was produced using a solution of fluticasone propionate in acetone (2.5% w/v) which was co-introduced with $CO_2$ at 100 bar, 75° C. and a flow rate ratio of 0.014 via a coaxial nozzle into the particle formation vessel. The particle shape is described as equant (FIG. 7).

EXAMPLE 3

Reproducibility

Three different solutions of fluticasone propionate in acetone (1.5% w/v) were co-introduced with $CO_2$ at 200 bar, 55° C. and a flow rate ratio of 0.029 via a coaxial to the particle formation vessel on three different days (Samples 6, 8, 9). The size, particle shape, polymorphic form and impurity profile were examined.

The particle size, particle shape, polymorphic form and impurity profile data show that the technique is reproducible when the same crystallising parameters are used.

a) Particle Size

The particle size was determined by laser diffraction (Malvern Mastersizer). The data are shown below in Table 3.

TABLE 3

| | Mean Particle size (μm) | % <5 μm | % <10 μm | Uniformity Index |
|---|---|---|---|---|
| Sample 6 | 9.7 | 24 | 51 | 10 |
| Sample 8 | 9.4 | 23 | 53 | 11 |
| Sample 9 | 9.6 | 23 | 52 | 12 | b) Particle Shape

The particle shape has been determined by scanning electron microscopy. Data for samples 6 and 8 are shown in FIGS. 6 and 8 respectively.

c) Polymorphic Form

Figure 9:
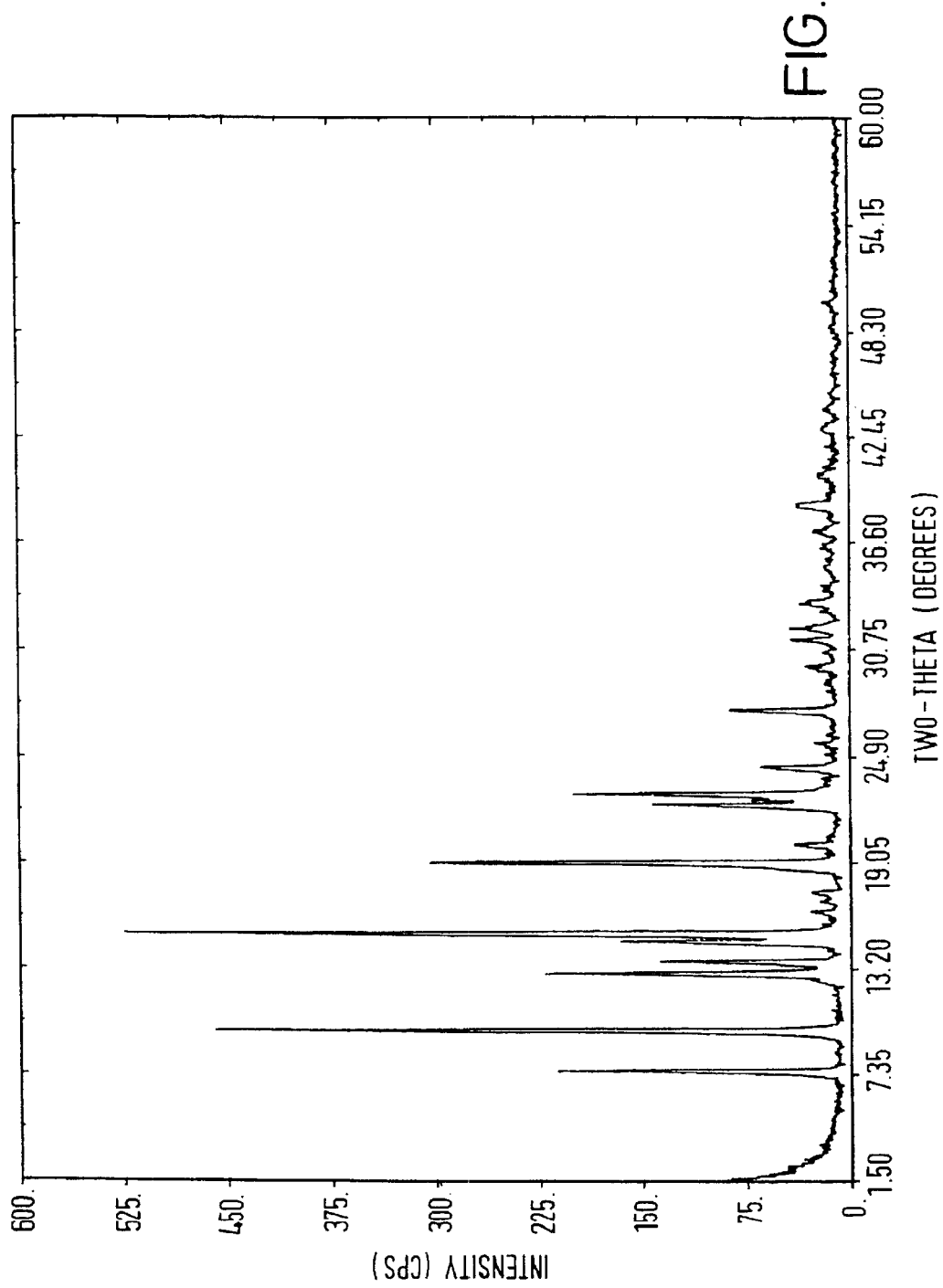
FIG. 9 is an X-ray powder diffraction (XRPD) pattern of fluticasone propionate, as prepared in Example 2.
Figure 10:
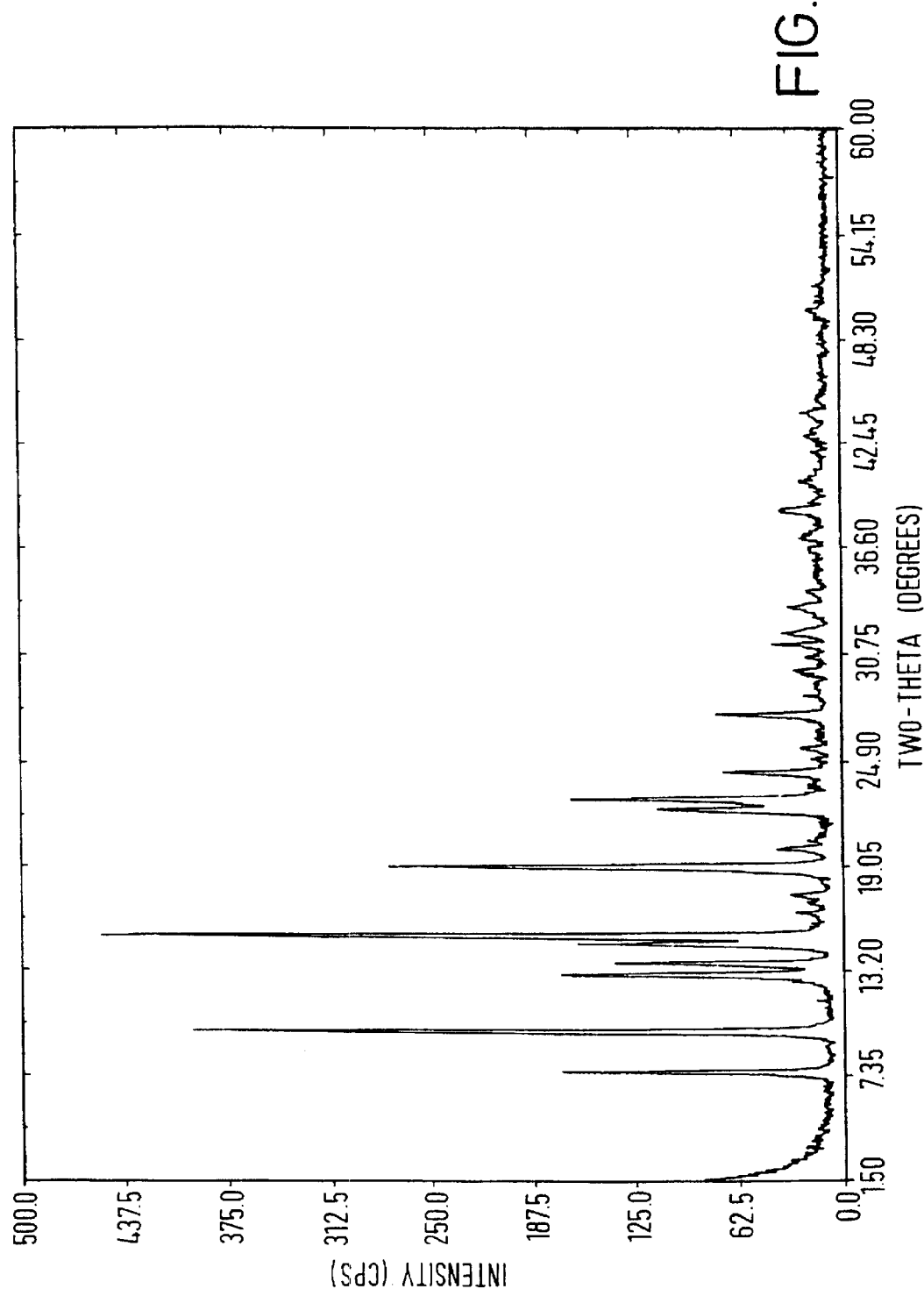
FIG. 10 is an X-ray powder diffraction (XRPD) pattern of fluticasone propionate, as prepared in Example 3.
Figure 11:
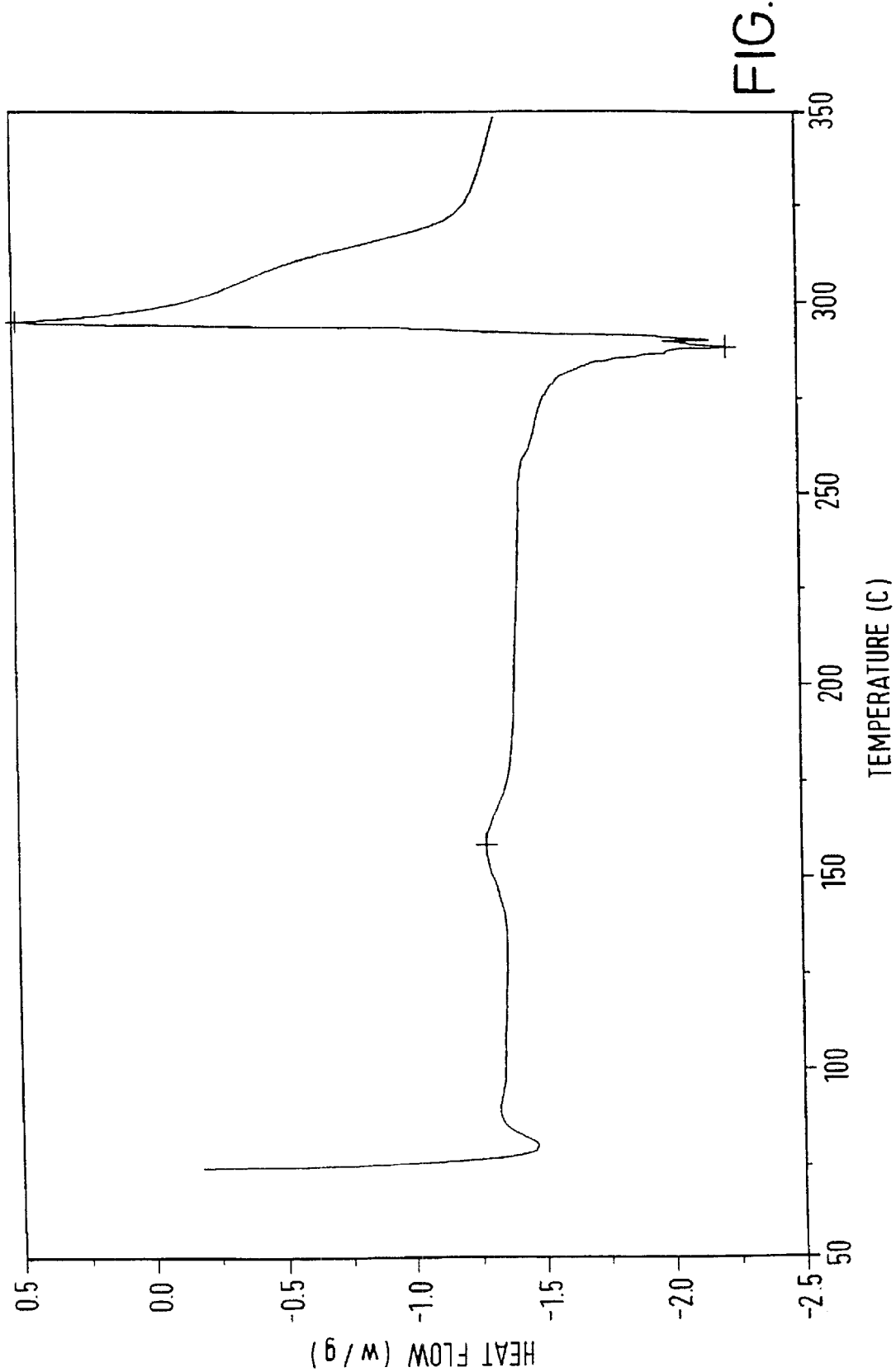
FIG. 11 is a differential scanning calorimetry (DSC) profile of fluticasone propionate, as prepared in Example 2.
Figure 12:
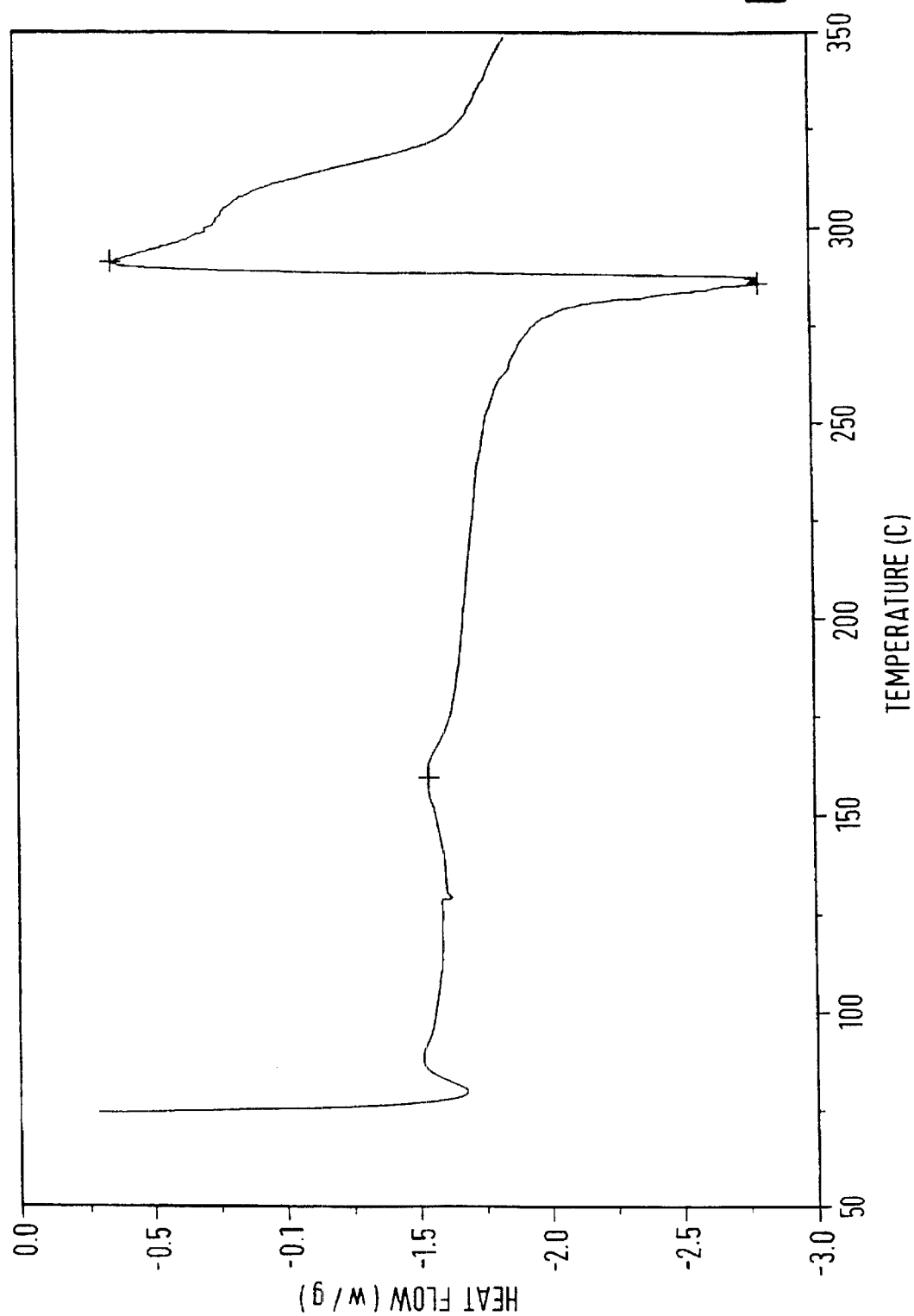
FIG. 12 is a differential scanning calorimetry (DSC) profile of fluticasone propionate, as prepared in Example 3.
Figure 13:
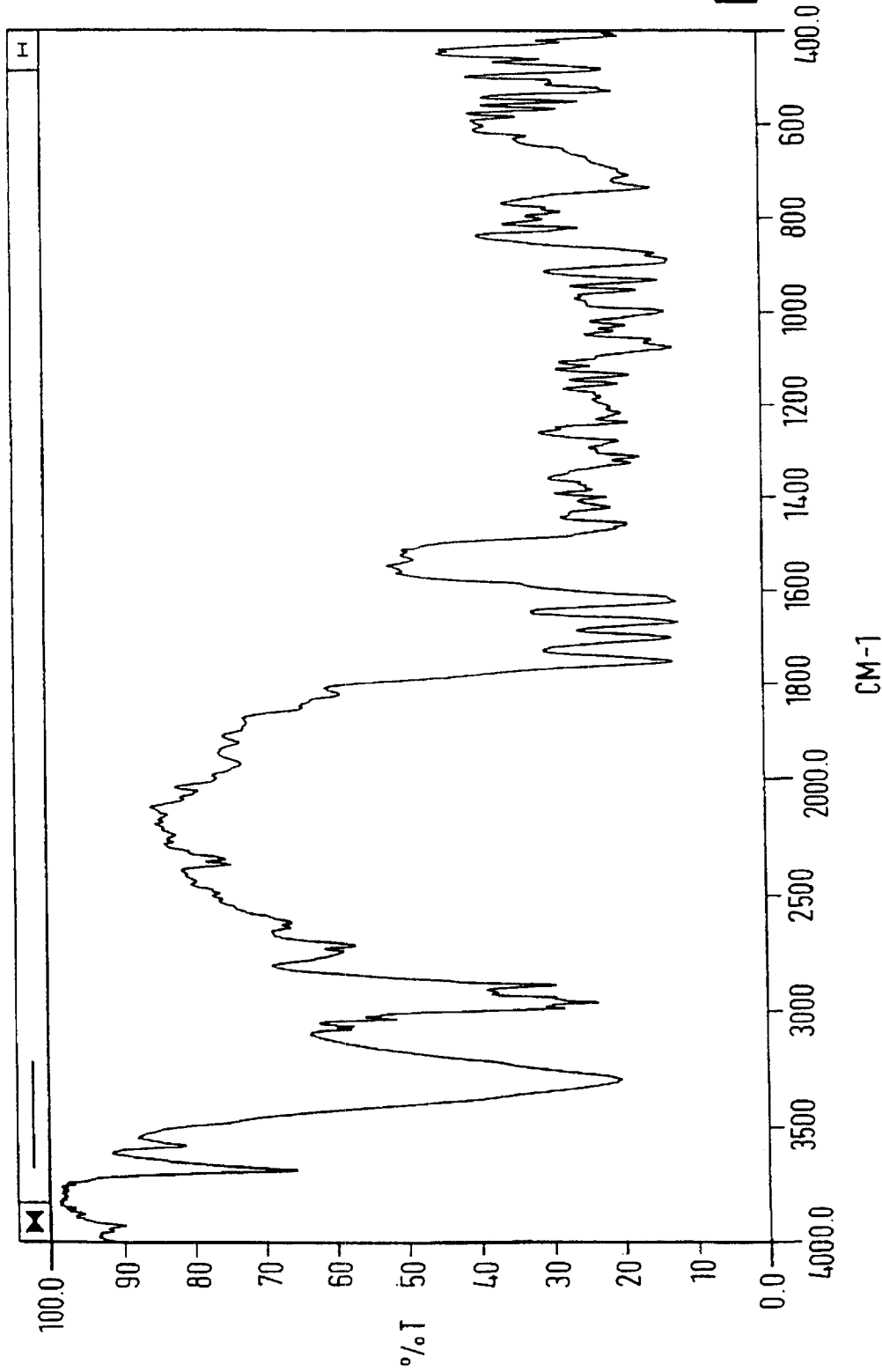
FIG. 13 is a fourier transform infra-red (FTIR) spectrum of fluticasone propionate, as prepared in Example 2.
Figure 14:
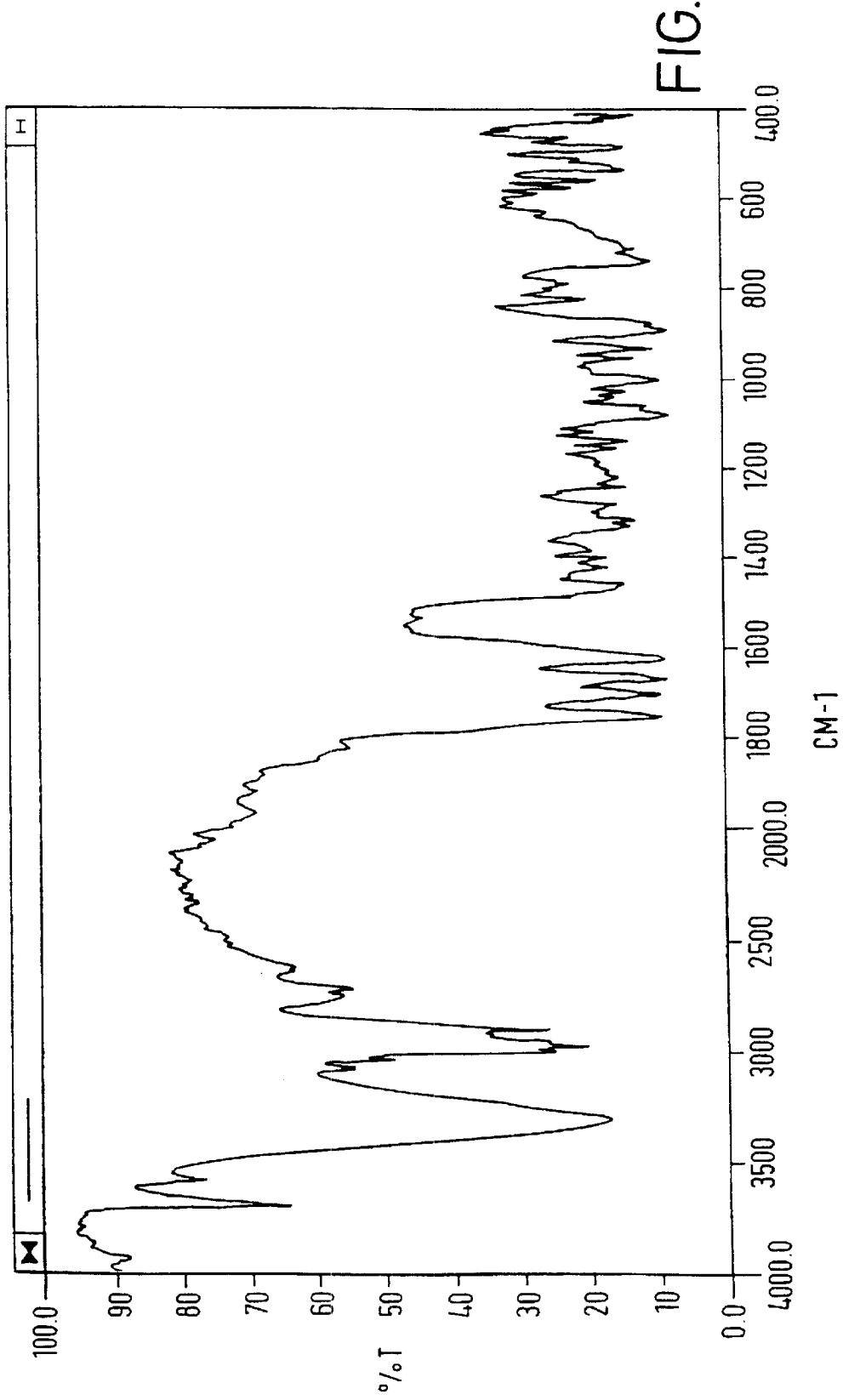
FIG. 14 is a fourier transform infra-red (FTIR) spectrum of fluticasone propionate, as prepared in Example 3.
Figure 15:
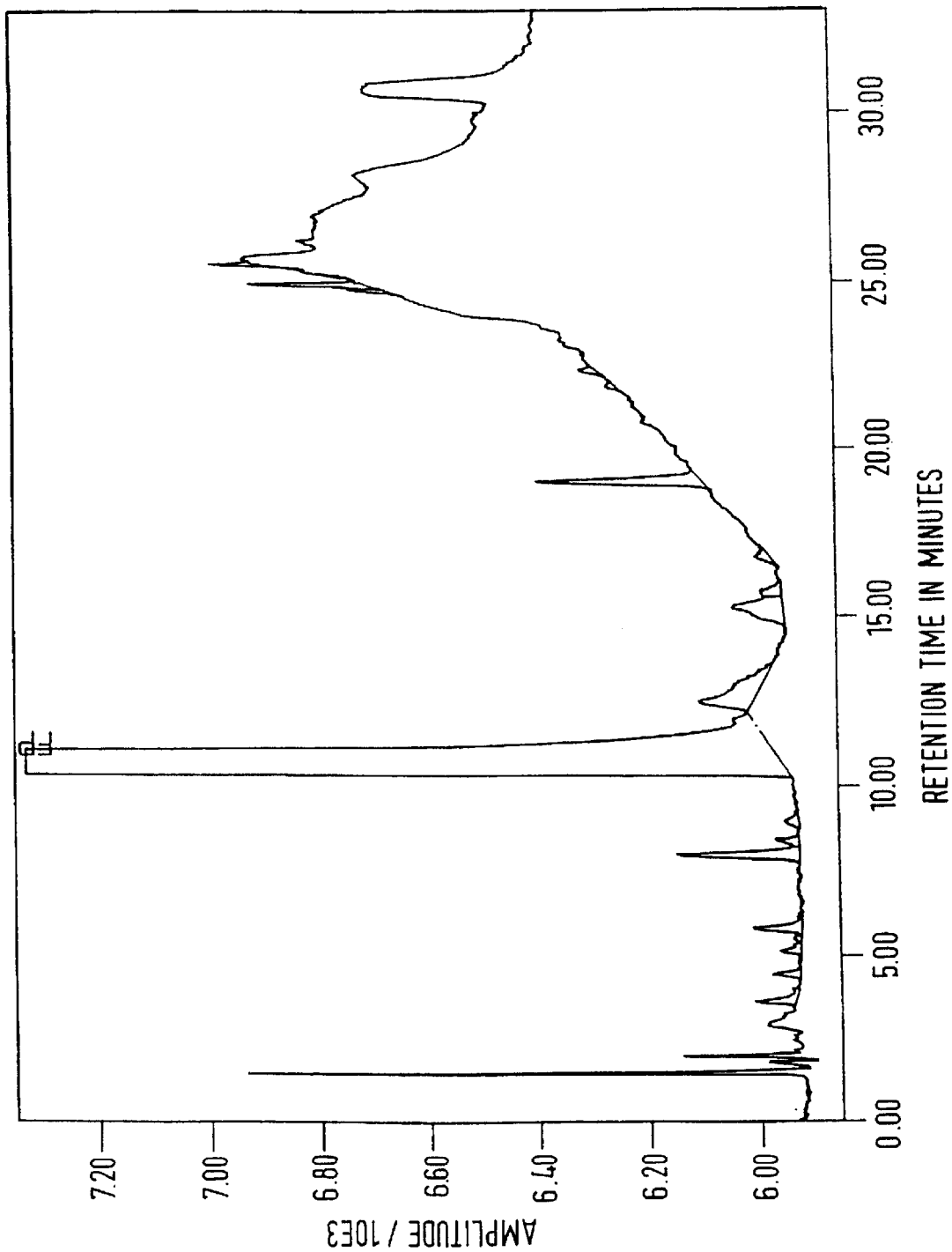
FIGS. 15 to 19 are HPLC chromatograms for the fluticasone propionate products as described in Example 4.

The polymorphic form has been determined by X-ray powder diffraction, differential scanning calorimetry (DSC) and fourier transform infra-red (FTIR) spectroscopy for samples 6 and 8. Data are shown in FIGS. 9 to 14. FIGS. 9, 11 and 13 relate to sample 6, whilst FIGS. 10, 12 and 14 relate to sample 8.

d) Impurity Profile

Figure 16:
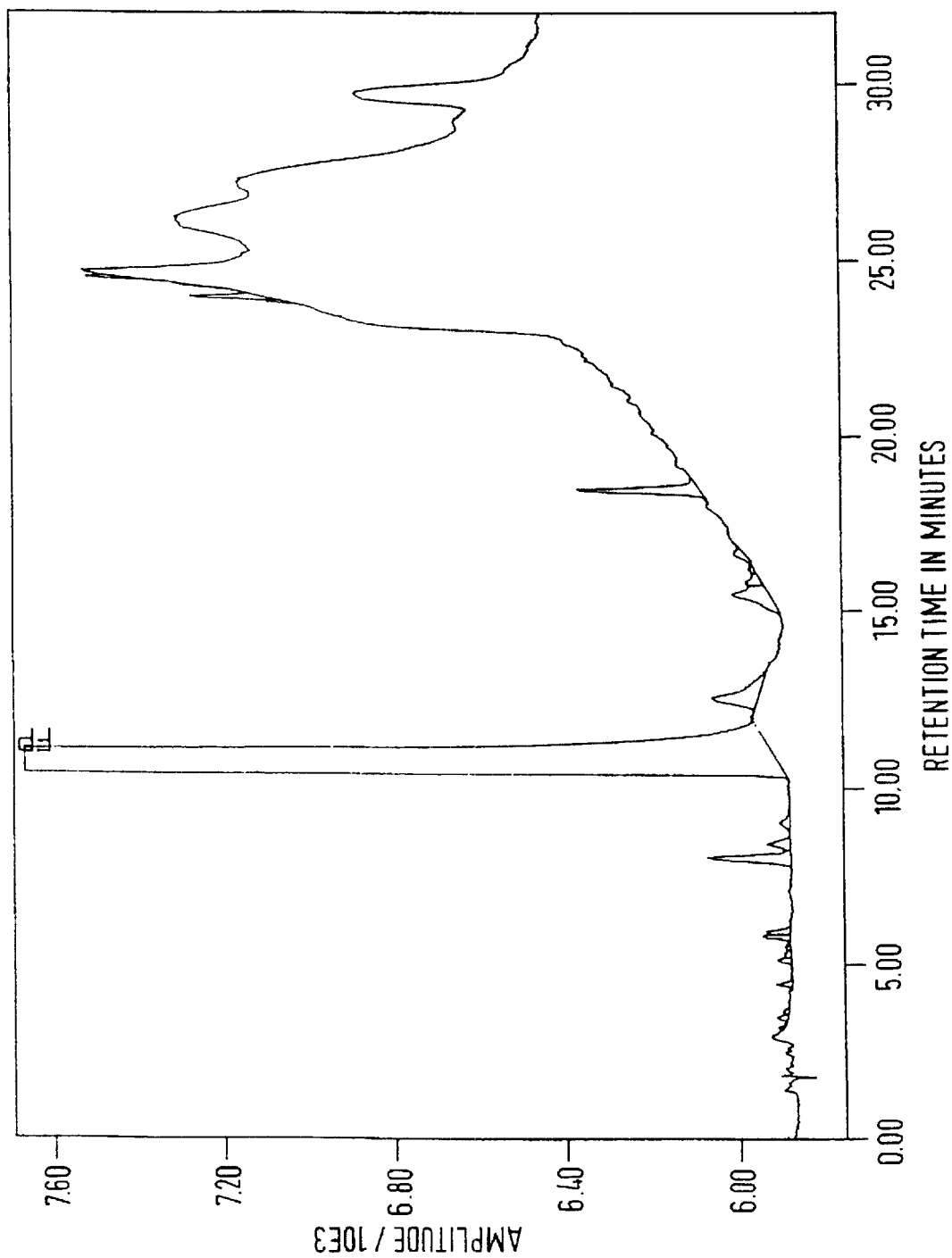
Figure 17:
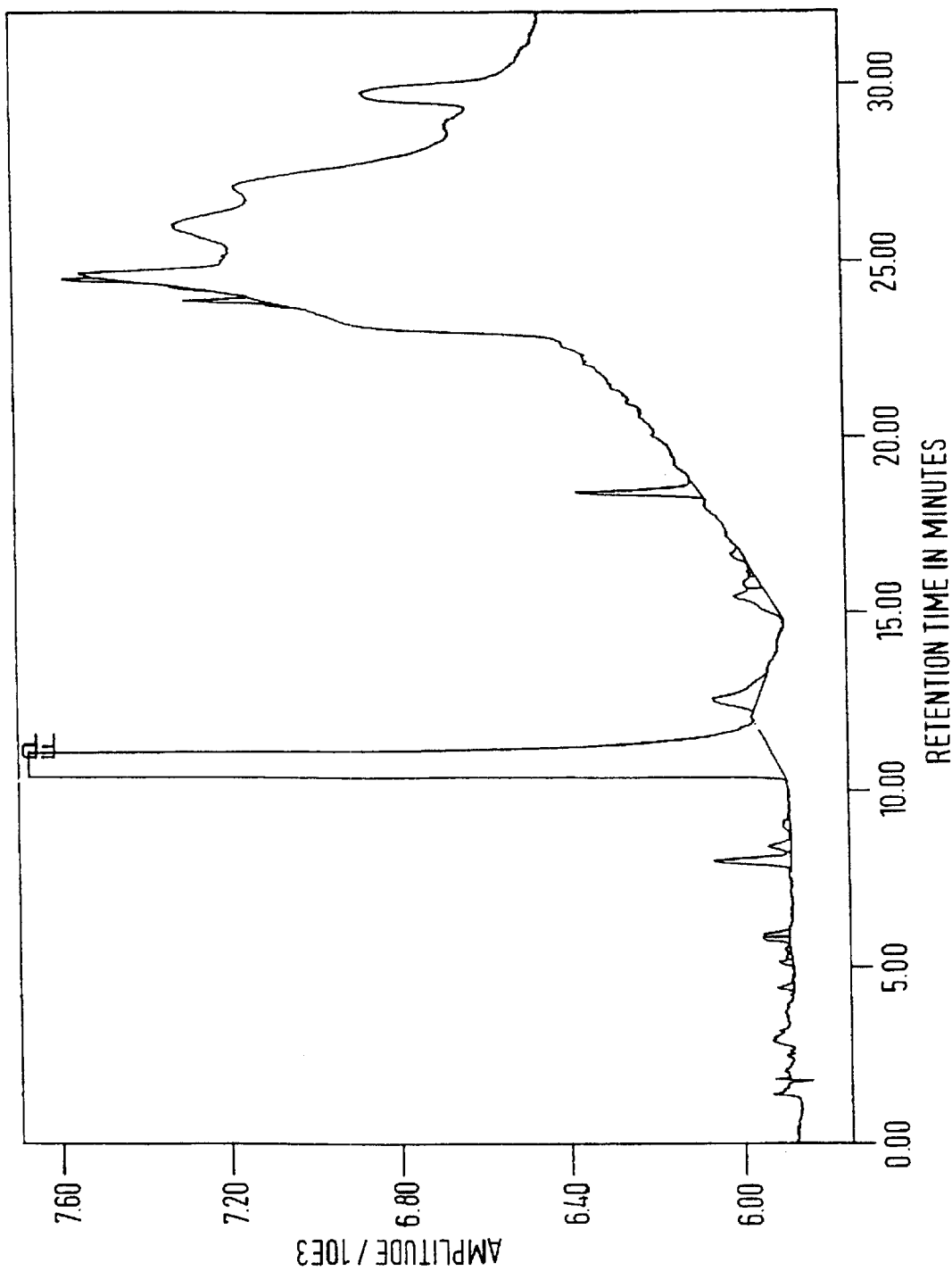
Figure 18:
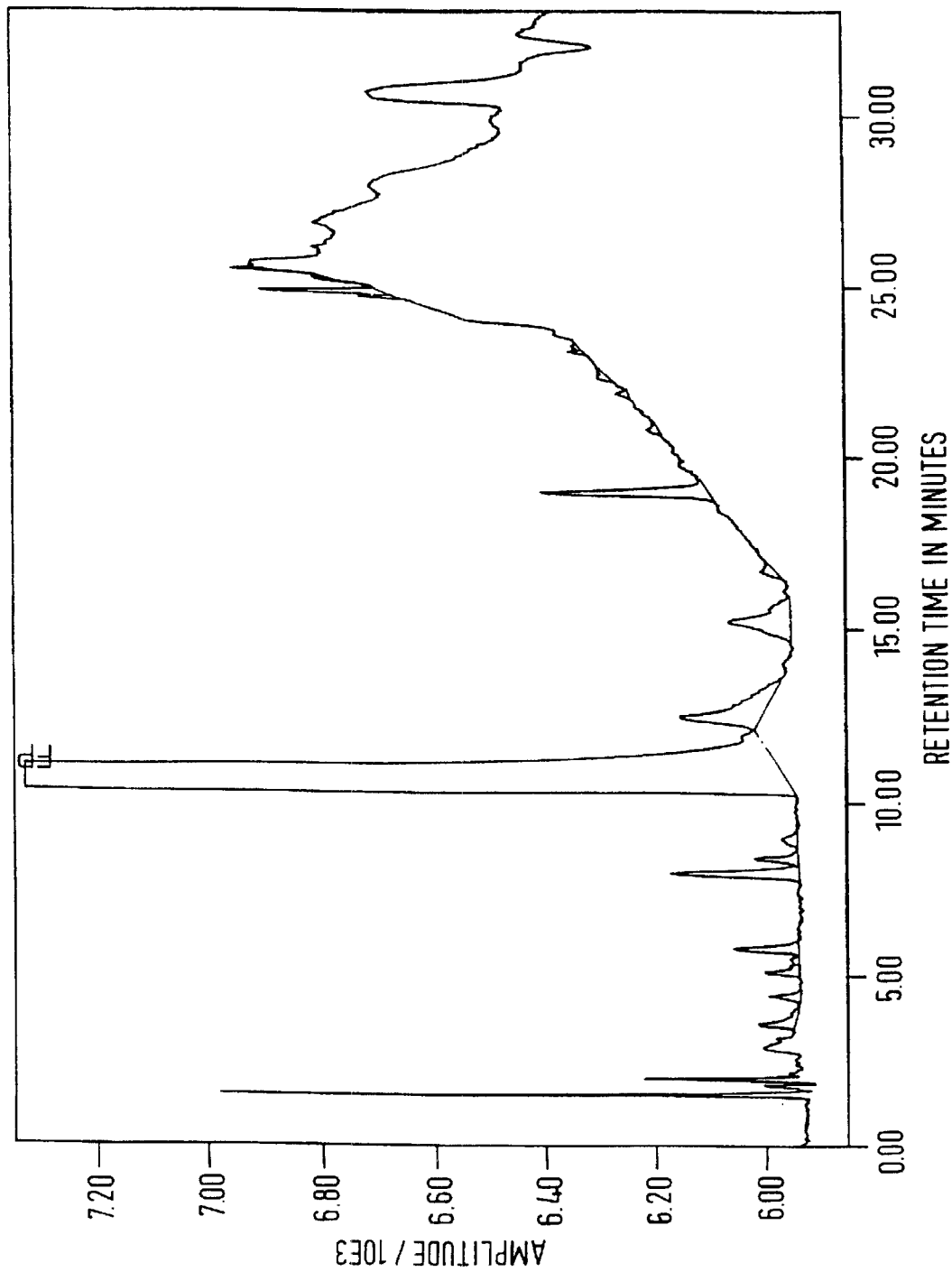
Figure 19:
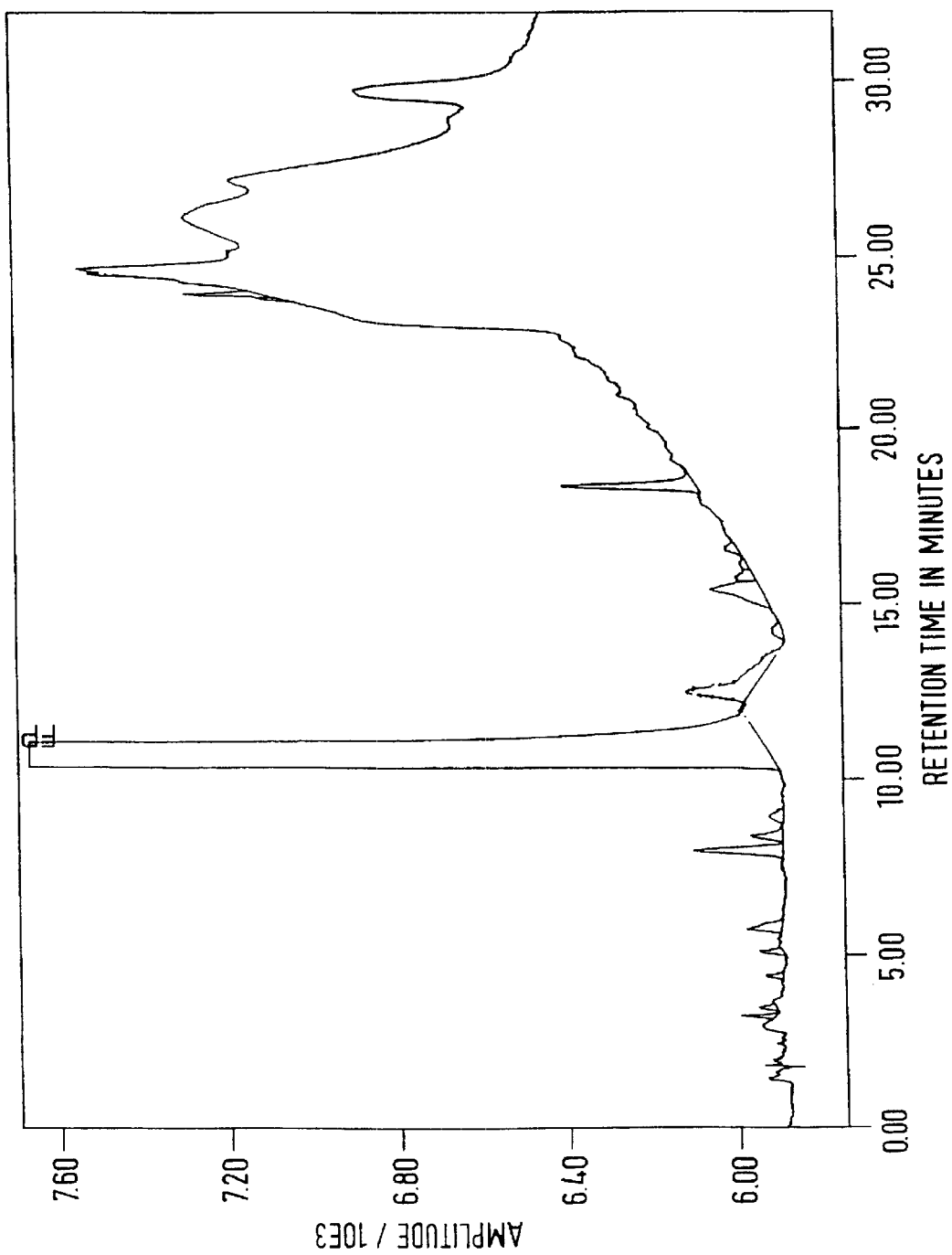
Figure 20:
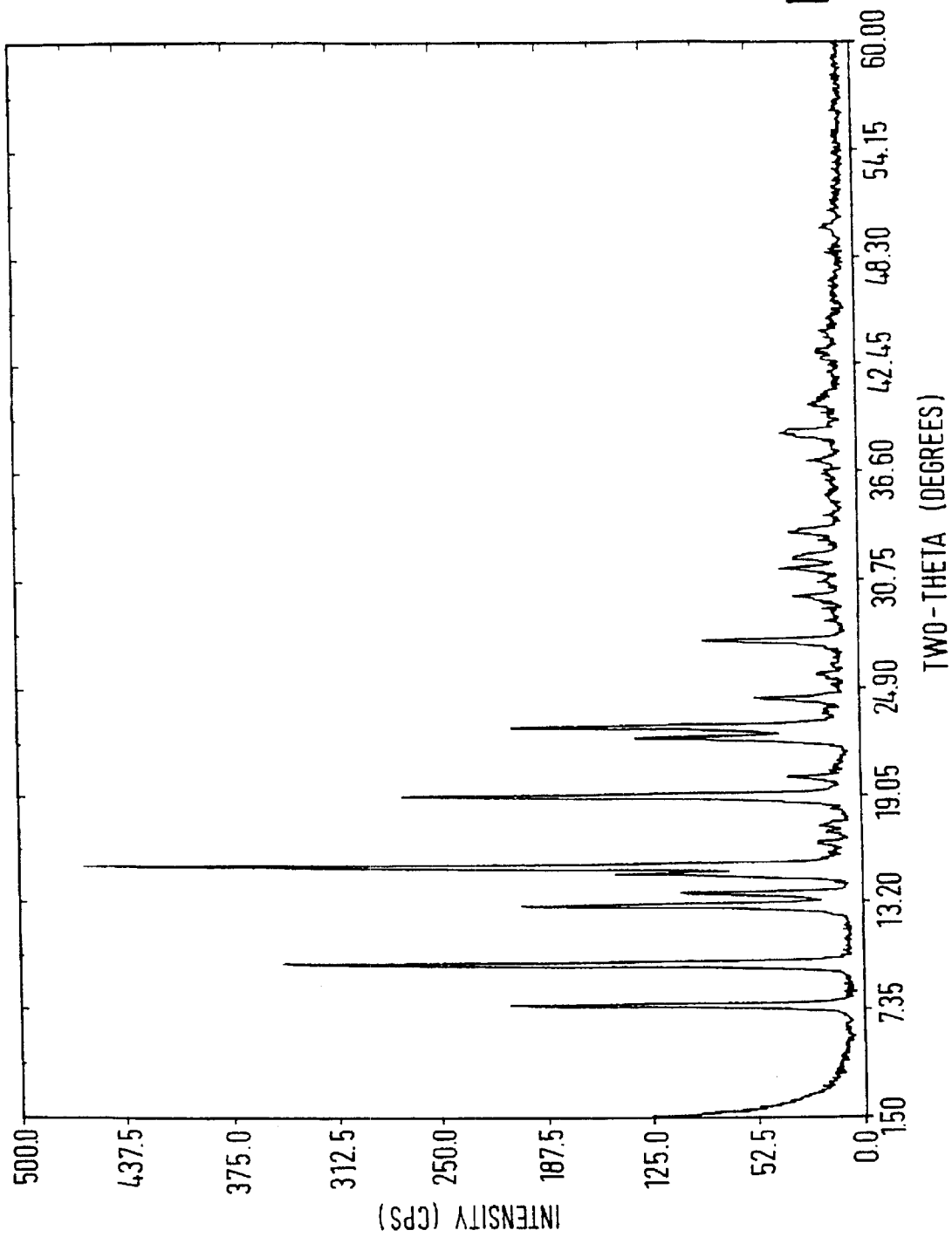
FIGS. 20 to 24 are XRPD patterns for the fluticasone propionate products as described in Example 5.
Figure 21:
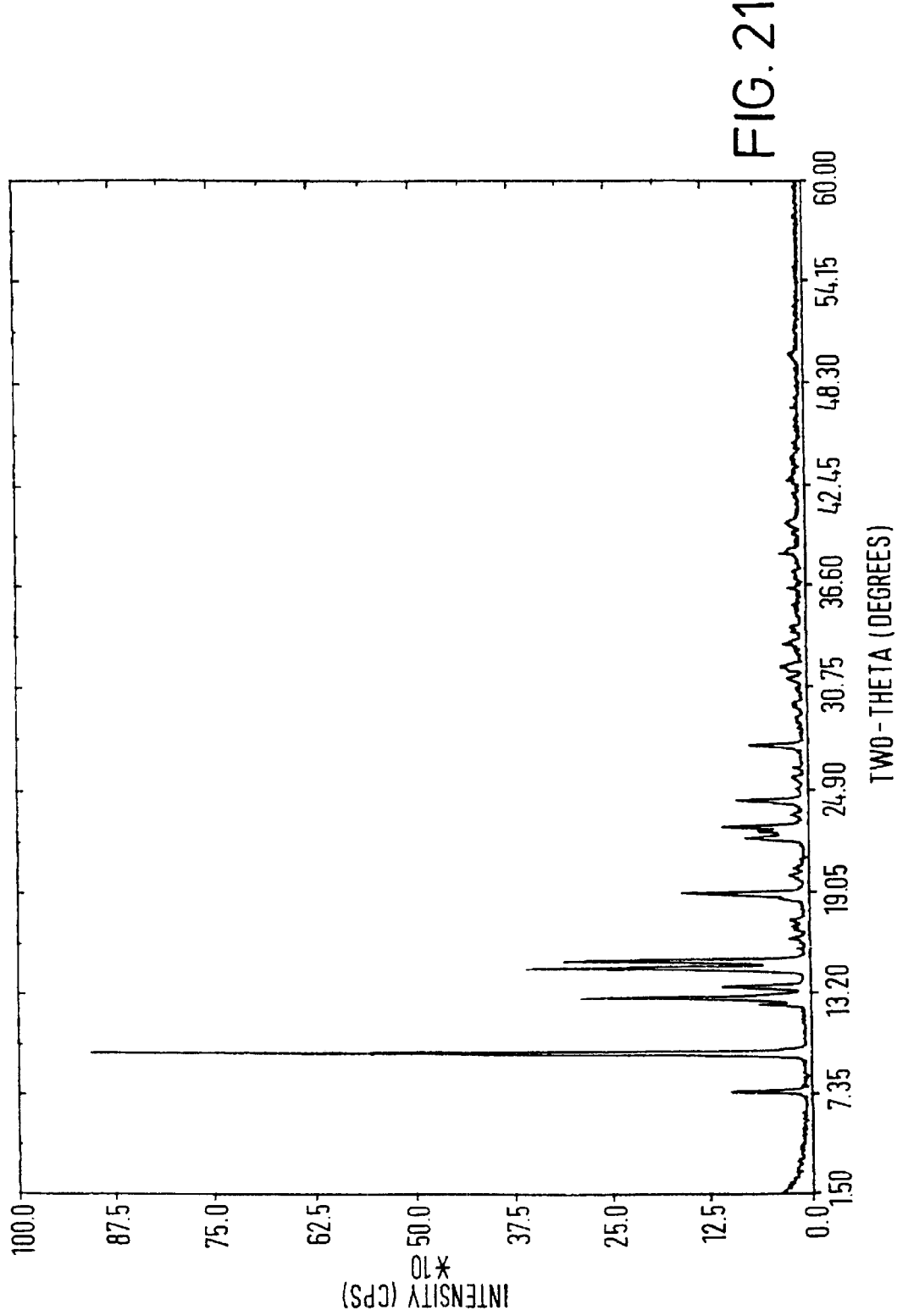
Figure 22:
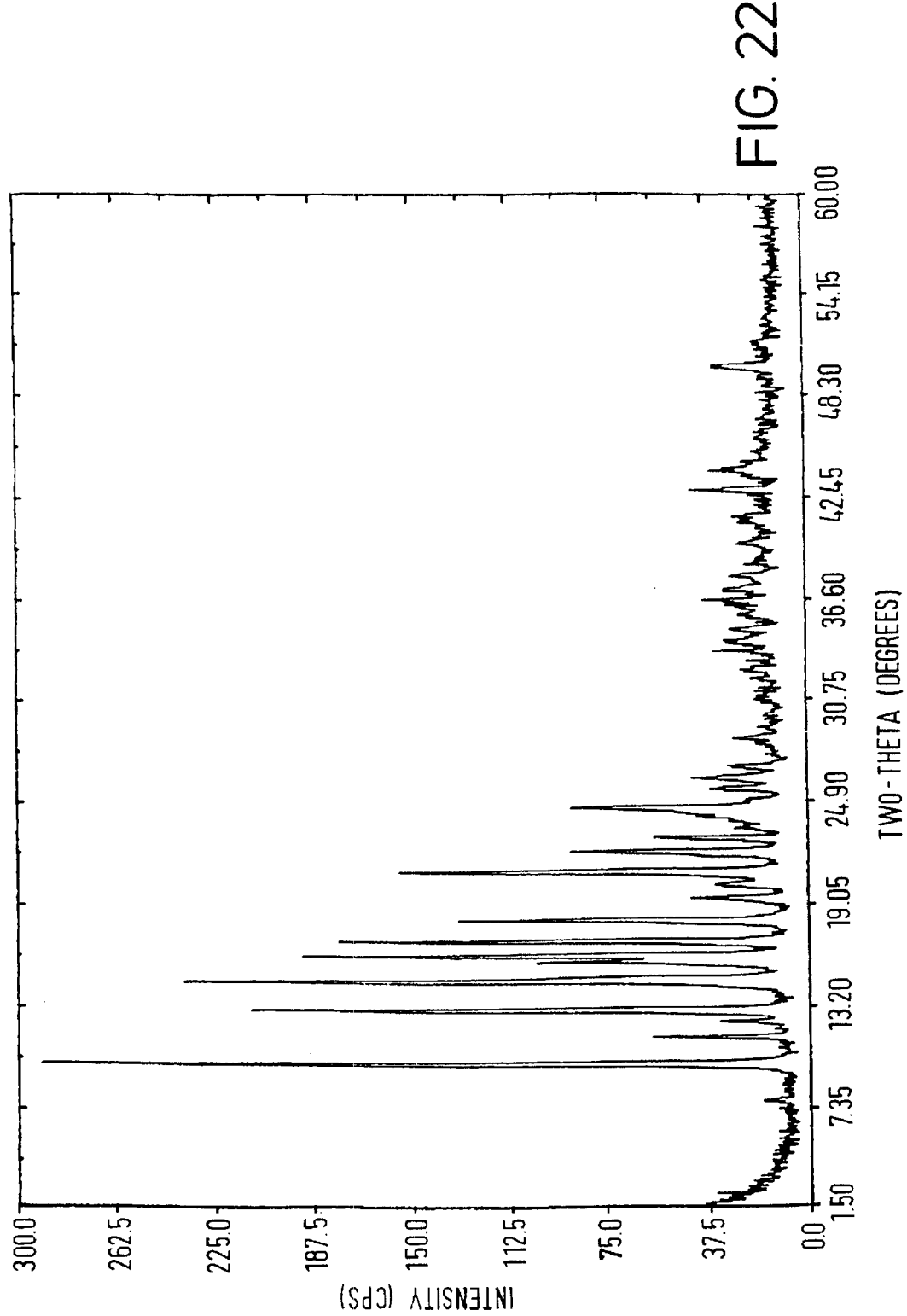

The impurity profile has been determined by HPLC for samples 6 and 8. The data are shown in Table 4 and FIGS. 16 and 17 (relating to samples 6 and 8 respectively).

EXAMPLE 4

Impurity Profile

The impurity profile has been determined by HPLC for samples 5, 6, 8, 10 and compared to conventionally crystallised fluticasone propionate. The data are shown in Table 4 and FIGS. 15 to 19 (which relate to samples 5, 6, 8, 10 and conventionally crystallised fluticasone propionate respectively).

Sample 10 was produced using a solution of fluticasone propionate in acetone (0.5% w/v) which was co-introduced with $CO_2$ at 300 bar, 35° C. and a flow rate ratio of 0.043 via a coaxial nozzle into the particle formation vessel.

The data show that fluticasone propionate produced by the present invention does not alter the impurity profile when compared to conventionally crystallised fluticasone propionate. However, there is a small reduction in the total impurities (% w/w) for fluticasone propionate produced by the present invention.

TABLE 4

| | Total Impurities (% w/w) | Most Abundant Impurity (% w/w) | 2nd most Abundant Impurity (% w/w) | Number of Impurities |
|---|---|---|---|---|
| Conventionally crystallised fluticasone propionate (micronised) | 0.60 | 0.20 | 0.14 | 5 |
| Sample 4 | 0.45 | 0.12 | 0.12 | 5 |
| Sample 6 | 0.51 | 0.14 | 0.12 | 5 |
| Sample 8 | 0.51 | 0.14 | 0.13 | 5 |
| Sample 10 | 0.59 | 0.17 | 0.14 | 5 |

(Note: Limit of quantification = 0.045% w/w)

EXAMPLE 5

Crystallinity and Polymorphism

X-ray powder diffraction (XRPD) patterns were generated using either a Siemens D 5000 or Philips X'pert MPD. The powders were scanned over a 2θ angle range of either 1.5° to 60°, or 0° to 35°, with a 0.02–0.050 step at 3–15 seconds count time using CuKα radiation. The Siemens D5000 measures intensity as counts per second and the Philips X'pert MPD measures intensity as counts.

Data for Samples 2, 6 and 11 were compared to those of conventionally crystallised fluticasone propionate. (See FIGS. 20, 9, 21 and 22 respectively.)

The production of Samples 2 and 6 is described above. Sample 11 was produced using a solution of fluticasone propionate in acetone (0.5% w/v) which was co-introduced with $CO_2$ at 300 bar, 75° C. and a flow rate ratio of 0.014 via a coaxial nozzle into the particle formation vessel.

The data show that the crystallinity can be controlled by the crystallisation parameters. Using the technique presented in the patent, the crystallinity of the fluticasone propionate can be improved significantly over conventionally crystallised fluticasone propionate.

As mentioned above, the relative amounts of Forms 1 and 2 of fluticasone propionate produced with the apparatus described herein may be altered by appropriate adjustment of the variables of the process of the invention. The experimental domains for each polymorphic form can be determined empirically for the particular apparatus employed. Using the preparative process and apparatus described herein, it was found that Samples 1, 2, 5–12 and 14–16 were Form 2 fluticasone propionate; Samples 3 and 17 were a mixture of Forms 1 and 2 fluticasone propionate; and Sample 13 is Form 1 fluticasone propionate.

Figure 23:
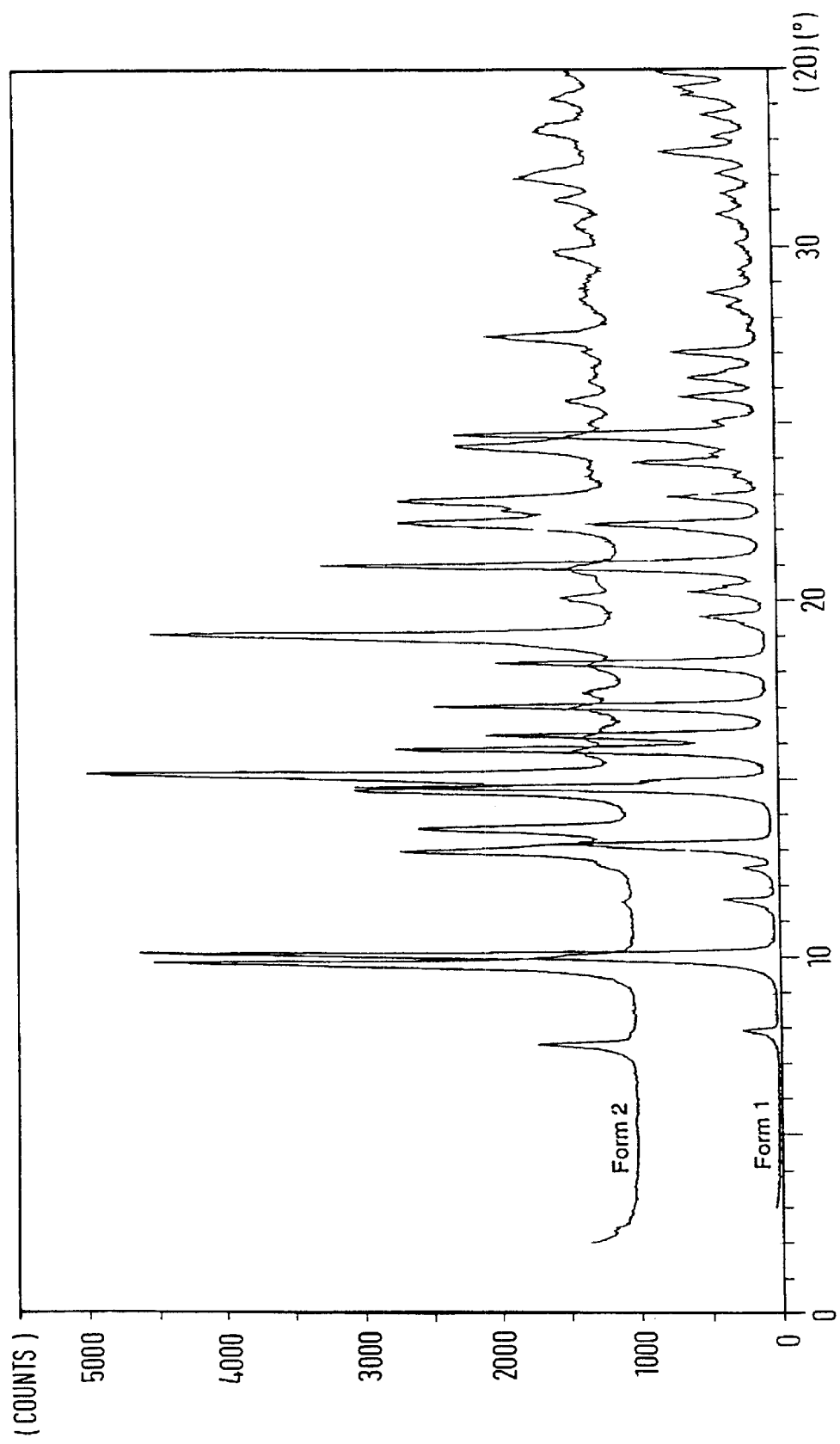

The two polymorphic forms of fluticasone propionate are well characterised by their XRPD traces. Table 5 shows the key 2θ peaks for identification of the two polymorphic forms of the fluticasone propionate by XRPD. FIG. 23 shows the XRPD traces of Forms 1 and 2 fluticasone propionate overlaid.

TABLE 5

| Polymorph | Primary Peaks (°) | | | | Secondary Peaks (°) | | | | |
| --- | --- | --- | --- | --- | --- | --- | --- | --- | --- |
| Form 1 | 7.9 | 10.0 | 11.5 | 12.4 | 13.1 | — | 14.9 | — | 15.8 |
| Form 2 | 7.6 | 9.8 | — | — | 13.0 | 13.6 | — | 15.2 | — |

Traces for the fluticasone propionate produced according to the present invention are qualitatively different from the trace for the conventionally crystallised fluticasone propionate. Conventionally crystallised fluticasone propionate ("Form 1") has been found to have a monoclinic crystal structure with $a=7.722$ Å, $b=14.176$ Å, $c=11.290$ Å, $\beta=98.458°$ In contrast, the XRPD traces of the fluticasone propionate produced according to the present invention ("Form 2") was analysed and proved to be a pure polymorph with an orthorhombic structure having $a=23.404$ Å, $b=14.048$ Å, $c=7.6953$ Å, all angles 90°

Figure 24:
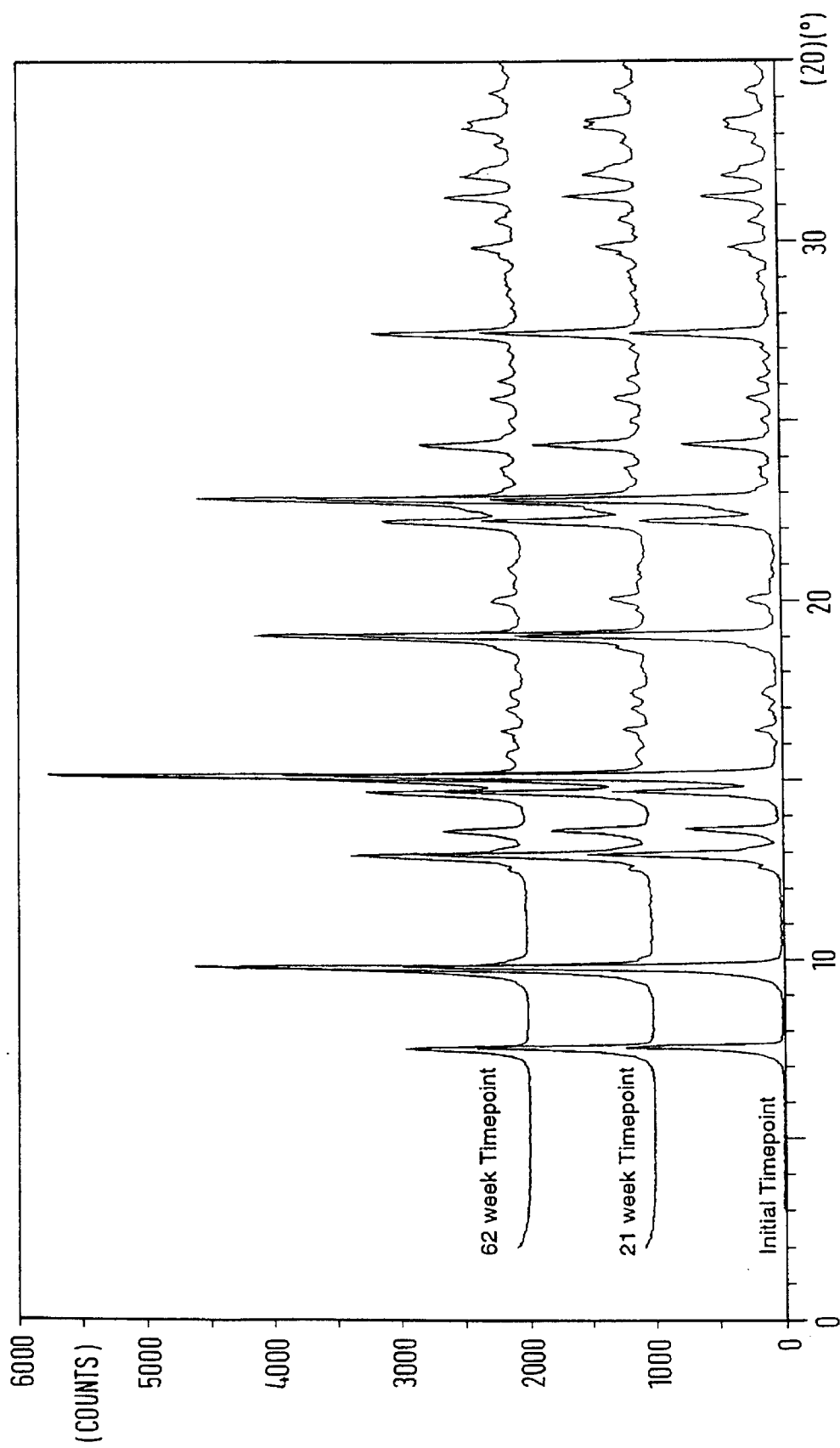

Form 2 was found to be stable to conversion to Form 1: after 62 weeks at ambient temperature and humidity, no conversion was seen. FIG. 24 shows the stability of Form 2 fluticasone propionate by XRPD.

The water content of the two crystalline forms of fluticasone propionate produced with the apparatus described herein has also been determined, and compared with that of conventionally crystallised and micronised fluticasone propionate. The results are shown in Table 6.

TABLE 6

| | Water content (% w/w) |
| --- | --- |
| Conventionally crystallised fluticasone propionate (micronised) | <0.1 |
| Form 1 fluticasone propionate prepared as described herein | <0.1 |
| Form 2 fluticasone propionate prepared as described herein | >0.3 |

EXAMPLE 6

Bulk Density

The dynamic bulk density for conventionally crystallised fluticasone propionate (micronised and non-micronised) and fluticasone propionate of the present invention are shown in Table 7.

Sample 12 was produced using a solution of fluticasone propionate in ethyl acetate (0.5% w/v) which was co-introduced with $CO_2$ at 300 bar, 35° C. and a flow rate ratio of 0.043 via a coaxial nozzle into the particle formation vessel.

Sample 13 was produced using a solution of fluticasone propionate in acetonitrile (0.5% w/v) which was co-introduced with $CO_2$ at 100 bar, 75° C. and a flow rate ratio of 0.043 via a coaxial nozzle into the particle formation vessel.

TABLE 7

| | Dynamic Bulk Density (W) g cm$^{-3}$ |
| --- | --- |
| Conventionally crystallised fluticasone propionate (micronised) | 0.21 |
| Conventionally crystallised fluticasone propionate (non-micronised) | 0.21 |
| Sample 12 | 0.05 |
| Sample 13 | 0.06 |
| Sample 3 | 0.17 |

The dynamic bulk density of fluticasone propionate of the present invention is significantly lower than for conventionally crystallised fluticasone propionate (micronised and non-micronised).

The data presented in Table 7 show that dynamic bulk density of fluticasone propionate of the present invention can be controlled using the crystallisation parameters of the method described within the patent.

EXAMPLE 7

Static Charge Test

The relative static charge of the fluticasone propionate of the present invention can be controlled by the crystallisation parameters. The data indicate there are no significant reductions in relative static of the fluticasone propionate of the present invention when compared to conventional micronised fluticasone propionate. Fluticasone propionate collected from the particle formation vessel using the apparatus described is dry and easily handled. Conventional micronised fluticasone propionate is cohesive, difficult to handle and statically charged.

A simple test was devised to ascertain a relative static charge based on the quantity of drug remaining coated to the walls of a vial after rolling a predetermined quantity of drug in the vial for 2 minutes. The greater the amount of the drug remaining on the vial, the higher the relative static charge associated with the drug substance. The results are displayed in Table 8.

TABLE 8

| Sample | % Drug retained on vial |
| --- | --- |
| Conventionally crystallised fluticasone propionate (micronised) | 4.5 |
| Sample 14 | 3.8 |
| Sample 15 | 4.2 |
| Sample 16 | 7.6 |
| Sample 17 | 8.6 |

Sample 14 was produced using a solution of fluticasone propionate in acetone (2.5% w/v) which was co-introduced with $CO_2$ at 300 bar, 75° C. and a flow rate ratio of 0.043 via a coaxial nozzle into the particle formation vessel.

Sample 15 was produced using a solution of fluticasone propionate in acetone (3.5% w/v) which was co-introduced with $CO_2$ at 90 bar, 85° C. and a flow rate ratio of 0.028 via a coaxial nozzle into the particle formation vessel.

Sample 16 was produced using a solution of fluticasone propionate in ethyl acetate (0.5% w/v) which was co-introduced with $CO_2$ at 300 bar, 35° C. and a flow rate ratio of 0.043 via a coaxial nozzle into the particle formation vessel.

Sample 17 was produced using a solution of fluticasone propionate in acetone (0.5% w/v) which was co-introduced with $CO_2$ at 100 bar, 75° C. and a flow rate ratio of 0.043 via a nozzle into the particle formation vessel.

EXAMPLE 8
Twin Impinger Test

A small quantity of drug was filled into each blister of a 4-blister Rotadisk™. The contents of each Rotadisk™ were emptied, via a Diskhaler™, into the Twin Impinger apparatus set to an airflow rate of 60 litres per minute. Each stage of the Twin Impinger apparatus contained a quantity of dissolving solvent, methanol, (stage 1, 7 ml and stage 2, 30 ml). The Rotadisk™ and Diskhaler™ were washed with methanol and the resultant solution made up to 50 ml. The stage 1 of the Twin Impinger was washed with methanol and the resultant solution made up to 50 ml. The stage 2 of the Twin Impinger was washed with methanol and the resultant solution made up to 50 ml. The solutions were assayed by UV spectrophotometry and the quantity of drug delivered to each stage of the Twin Impinger apparatus calculated. The results are displayed in Table 9. Table 10 displays the size data of the samples used.

TABLE 9

Drug Deposition as % of Total Drug Recovered

|  | Device | Stage 1 | Stage 2 | Delivered Dose |
|---|---|---|---|---|
| Conventionally crystallised fluticasone propionate (micronised) | 40 | 43 | 17 | 60 |
| Sample 15 | 36 | 47 | 17 | 64 |
| Sample 16 | 28 | 58 | 14 | 72 |

TABLE 10

|  | Mean Particle size (μm) | % <5 μm | % <10 μm | Uniformity Index |
|---|---|---|---|---|
| Sample 15 | 4.0 | 61 | 84 | 7 |
| Sample 16 | 8.4 | 27 | 59 | 13 |

The stage 2 deposition represents the fine particle mass (respirable dose) reaching the deep lung. The delivered dose (sum of stage 1 and stage 2) represents the total dose available for inhalation and the emptying efficiency of the drug from the device.

Fluticasone propionate of the present invention shows no significant improvement in stage 2 deposition. An interesting feature of the present invention is that the supercritical fluid crystallised fluticasone propionate with a particle size greater than that of conventionally crystallised fluticasone propionate (micronised) gives an equivalent deposition (respirable dose) in the stage 2 of the Twin Impinger.

Fluticasone propionate of the present invention shows an improved delivered dose indicating the drug is emptied well from the device and is presenting a greater quantity of drug for inhalation. Again it is an interesting feature of the present invention that the supercritical fluid crystallised fluticasone propionate with a particle size greater than that of conventionally crystallised fluticasone propionate (micronised) gives a greater delivered dose.

These data indicate that fluticasone propionate of the present invention has improved fluidisability and flow properties.

EXAMPLE 9
Solvent Content Test

The solvent content of fluticasone propionate of the present invention was investigated by Nuclear Magnetic Resonance (NMR) and compared to that of conventional crystallised fluticasone propionate. Each sample was tested for acetone content. (The conventionally crystallised fluticasone propionate was crystallised from acetone.) In addition, sample 5 was crystallised from methanol and therefore tested for methanol. Table 11 displays the solvent content data for each sample.

TABLE 11

|  | Acetone Content (% w/w) | Methanol Content (% w/w) |
|---|---|---|
| Conventionally crystallised fluticasone propionate (micronised) | typically 0.7 | N/A |
| Sample 5 | Not Detected | Not Detected |
| Sample 8 | Not Detected | N/A |
| Sample 15 | Not Detected | N/A |

The data indicate that there are no detectable levels of residual solvent within the fluticasone propionate of the present invention. Lack of residual solvent in the samples is consistent with GAS (Gas Anti-Solvent) recrystallisation and RESS (Rapid Expansion of Supercritical Solutions).

The benefits of no residual solvent within the sample may include: improved stability due to lack of solvent-drug interactions on temperature and humidity storage; reduced crystal imperfections and improved crystal structure due to lack of solvent occlusions.

EXAMPLES 10–12
Performance of Metered Dose Inhalers

In the following tests, two types of metered dose inhaler (MDI) were manufactured, both containing fluticasone propionate and HFA134a. Inhaler Type A was a 125 microgram, 120 actuation model. Inhaler Type B was a 50 microgram, 120 actuation model.

Inhalers Type A were prepared by dispensing 20 mg drug into an 8 ml Presspart aluminium can. The can was closed by crimping on a Valois DF60 63 microlitre Valve before pressure-filling the canister with 12 g of Propellent HFA134a. Inhalers Type B were prepared in the same way but employing only 8 mg drug.

The performance of MDI's has been measured based on drug deposition on the can, valve and actuator; dose delivered through use; and respirable dose.

The following crystallisation conditions were used in preparing samples for filling into the aforementioned MDI's.

Sample 18 was produced using a solution of fluticasone propionate in acetonitrile (2.0% w/v) which was co-introduced with $CO_2$ at 300 bar, 35° C. and a flow rate ratio of 0.043 via a coaxial nozzle into the particle formation vessel.

Sample 19 was produced using a solution of fluticasone propionate in acetone (2.5% w/v) which was co-introduced with $CO_2$ at 100 bar, 35° C. and a flow rate ratio of 0.043 via a coaxial nozzle into the particle formation vessel.

Sample 20 was produced using a solution of fluticasone propionate in acetone (2.5% w/v) which was co-introduced with $CO_2$ at 100 bar, 35° C. and a flow rate ratio of 0.014 via a coaxial nozzle into the particle formation vessel.

Sample 21 was produced using a solution of fluticasone propionate in acetone (2.5% w/v) which was co-introduced with $CO_2$ at 100 bar, 35° C. and a flow rate ratio of 0.033 via a coaxial nozzle into the particle formation vessel.

Sample 22 was produced using a solution of fluticasone propionate in acetonitrile (2.0% w/v) which was co-introduced with $CO_2$ at 100 bar, 35° C. and a flow rate ratio of 0.022 via a coaxial nozzle into the particle formation vessel.

EXAMPLE 10

Drug Deposition

The drug deposited on the can, valve and actuator were measured at the beginning of use of the inhaler (after actuations 1 & 2) and at the end of use of the inhaler (after actuations 119 & 120). After the appropriate number of actuations, the inhaler exterior is washed in acetonitrile to remove any residual drug deposited on the surface. The drug found on the actuator is washed into a suitable container with 50 ml acetonitrile/water (50:50 v/v). The inhaler is then frozen in liquid nitrogen, the valve removed quickly and the contents of the drug suspension emptied into a suitable container. The propellant from the suspension is allowed to evaporate and the drug remaining is dissolved in 50 ml acetonitrile/water (50:50 v/v). The drug on the valve components is washed into a suitable container with 50 ml acetonitrile/water (50:50 v/v). The drug on the can is also washed into a suitable container with 50 ml acetonitrile/water (50:50 v/v). The resultant solutions are assayed by HPLC.

Tables 12 and 13 present the drug deposition profile for Inhalers Types A and B respectively.

Fluticasone propionate of the present invention shows significantly lower drug deposition on the can, valve and actuator than conventionally produced fluticasone propionate. As a result of the lower drug deposition, the concentration of drug in the suspension is higher, leading to higher quantities of drug being delivered from the inhaler. This is confirmed in Examples 11 (Dose Through Use) and 12 (Cascade Impactor Testing), which show higher dose delivery through the life of the inhaler.

TABLE 12

Drug Deposition Profile for Inhaler Type A

| Drug | Conventionally crystallised fluticasone propionate (micronised) | Fluticasone propionate of the present invention (sample 18) | Fluticasone propionate of the present invention (sample 20) |
|---|---|---|---|
| Amount of drug in Suspension (mg) | 17.7 | 18.1 | 18.9 |
| Can Deposition at the beginning of use (mg) | 1.0 | 0.8 | 0.5 |
| Valve Deposition at the beginning of use (mg) | 0.7 | 0.5 | 0.3 |
| Total Drug Deposition at the beginning of use (mg) | 1.7 | 1.3 | 0.8 |
| Actuator Deposition at the beginning of use (micrograms) | 15 | 12 | 11 |

TABLE 13

Drug Deposition Profile for Inhaler Type B

| Drug | Conventionally crystallised fluticasone propionate (micronised) | Fluticasone propionate of the present invention (sample 21) | Fluticasone propionate of the present invention (sample 22) |
|---|---|---|---|
| Amount of drug in Suspension (mg) | 6.4 | 7.1 | 7.3 |
| Can Deposition at the beginning of use (mg) | 0.5 | 0.4 | 0.3 |
| Can Deposition at the end of use (mg) | 0.6 | 0.4 | 0.3 |
| Valve Deposition at the beginning of use (mg) | 0.2 | 0.2 | 0.2 |
| Valve Deposition at the end of use (mg) | 0.5 | 0.3 | 0.2 |
| Total Drug Deposition at the beginning of use (mg) | 0.7 | 0.6 | 0.5 |
| Total Drug Deposition at the end of use (mg) | 1.1 | 0.7 | 0.5 |

Fluticasone propionate of the present invention also shows no significant increase in the drug deposition on the can and valve through the life of the inhaler. As a result, the delivery dose is consistent through the life of the inhaler as shown in the following Example.

EXAMPLE 11

Dose Delivered Through Use

The dose delivered through use of the inhalers has been measured on Inhaler Type B. Doses are collected as pairs of actuations at the beginning of use (actuations 1 & 2), the middle of use (actuations 60 & 61) and the end of use (actuations 119 & 120. The doses are collected as follows: The two actuations are fired into a 500 ml separating funnel (plugged at one end with cotton wool) which has a 20 litre per minute airflow pulled through it. The separating funnel is washed with acetonitrile into a 100 ml volumetric flask containing 50 ml of water. The resultant solution is made up to volume and assayed by HPLC.

Table 14 presents the Dose Delivered Through Use data for Inhaler Type B, for which the target dose to be delivered is 44 micrograms per actuation.

TABLE 14

Dose Delivered Through Use for Inhaler Type B

| Drug | | Beginning of use (Actuations 1 & 2) | Middle of use (Actuations 60 & 61) | End of use (Actuations 119 & 120) |
|---|---|---|---|---|
| Conventionally crystallised propionate (micronised) | Mean (mcg) | 31.3 | 35.9 | 39.3 |
| | RSD (%) | 4.2 | 6.5 | 9.2 |
| Fluticasone propionate of the present | Mean (mcg) | 44.3 | 47.9 | 46.0 |

TABLE 14-continued

Dose Delivered Through Use for Inhaler Type B

| Drug | | Beginning of use (Actuations 1 & 2) | Middle of use (Actuations 60 & 61) | End of use (Actuations 119 & 120) |
|---|---|---|---|---|
| invention (sample 22) | RSD (%) | 4.2 | 6.8 | 6.3 |

Fluticasone propionate of the present invention shows a dosing profile through the life of the inhaler which is consistently close to the target dose of 44 micrograms. This profile is significantly better than that of conventionally crystallised fluticasone propionate (micronised) which shows a significant increase in dose per actuation through use of the inhaler.

The dose variability at each point through the use of the inhaler for fluticasone propionate of the present invention is comparable with that of conventionally crystallised fluticasone propionate (micronised) but shows an improvement towards the end of the use of the inhaler.

The delivered dose for fluticasone propionate of the present invention is consistently higher than that of conventionally crystallised fluticasone propionate (micronised), due to the lower drug deposition on the can and valve as shown in Example 10.

EXAMPLE 12

Cascade Impactor Test

Cascade Impaction testing was performed on Inhaler Type A. The method used was in accordance with "Preparations for Inhalation; Aerodynamic assessment of fine particles using apparatus D" as defined in the British Pharmacopoeia 1993, Addendum, 1996, page A527 as applied to a metered dose inhaler formulation.

Data for Cascade impaction are presented in Table 15 below for a batch of inhalers made using the material from sample 19 and compared to inhalers made using conventionally crystallised and micronised material.

The deposition in stages 3, 4 and 5 represents the fine particle mass reaching the deep lung. The delivered dose (ex actuator) represents the total dose available for inhalation and the emptying efficiency of the drug from the device.

TABLE 15

Cascade Impaction Data for Inhaler Type A

| | Quantity of Drug Deposited on Each Stage of the Cascade Impactor (micrograms) | |
|---|---|---|
| | Conventionally crystallised fluticasone propionate (micronised) | Fluticasone propionate of the present invention (sample 19) |
| Mean particle Size (microns) | 1.8 | 4.8 |
| Actuator | 13.6 | 13.8 |
| Throat | 46.8 | 42.2 |
| Stage 0 | 5.7 | 10.9 |
| Stage 1 | 2.4 | 3.7 |
| Stage 2 | 3.8 | 3.9 |
| Stage 3 | 15.3 | 11.5 |
| Stage 4 | 19.2 | 17.1 |
| Stage 5 | 11.5 | 18.0 |
| Stage 6 | 1.2 | 2.7 |

TABLE 15-continued

Cascade Impaction Data for Inhaler Type A

| | Quantity of Drug Deposited on Each Stage of the Cascade Impactor (micrograms) | |
|---|---|---|
| | Conventionally crystallised fluticasone propionate (micronised) | Fluticasone propionate of the present invention (sample 19) |
| Stage 7 | 0.4 | 0.6 |
| Filter | 0.3 | 0.3 |
| Delivered dose Ex Valve | 119.9 | 124.5 |
| Delivered dose Ex Actuator | 106.3 | 110.8 |
| Fine particle Mass | 46.0 | 46.6 |
| Mass Median Aerodynamic diameter | 3.1 | 3.0 |
| Geometric standard deviation | 1.7 | 1.9 |

Fluticasone propionate of the present invention shows no significant improvement in fine particle mass. The interesting feature of the present invention is that the supercritical fluid crystallised fluticasone propionate with a particle size greater than that of conventionally crystallised fluticasone propionate (micronised) gives an equivalent fine particle mass in the Cascade Impactor.

Fluticasone propionate of the present invention shows an improved delivered dose indicating that the drug is emptied well from the device and is presenting a greater quantity of drug for inhalation. This is being aided by the lower drug can/valve deposition, which increases the concentration of drug in the suspension. Again, the interesting feature of the present invention is that the supercritical fluid crystallised fluticasone propionate with a particle size greater than that of conventionally crystallised fluticasone propionate (micronised) gives a greater delivered dose.

The data indicate that fluticasone propionate of the present invention has improved fluidisability and flow properties.

What is claimed is:

1. S-fluoromethyl 6α,9α-difluoro-11β-hydroxy-16α-methyl-3oxo-17α-propionyloxyandrosta-1,4-diene-17β-carbothiate (fluticasone propionate) having an orthorhombic crystalline structure and in a form with a dynamic bulk density of less than 0.2 g cm$^{-3}$.

2. Fluticasone propionate as claimed in claim 1 with a dynamic bulk density in the range between 0.05 and 0.17 g cm$^{-3}$.

3. Fluticasone propionate as claimed in claim 2 with a dynamic bulk density in the range between 0.05 and 0.08 g cm$^{-3}$.

4. Fluticasone propionate as claimed in claim 1 which has a particle size in the range of 1 to 10 microns.

5. Fluticasone propionate as claimed in claim 1 which has a uniformity coefficient of from 1 to 20.

6. Fluticasone propionate as claimed in claim 1 which has a respirable fraction of 14% or more by weight.

7. Fluticasone propionate as claimed in claim 1 which has a cohesivity of 0 to 20%.

8. Fluticasone propionate as claimed in claim 7 which has a cohesivity of 0 to 10%.

9. A pharmaceutical composition comprising fluticasone propionate as claimed in claim 1 together with at least one pharmaceutically acceptable carrier or excipient.

10. A pharmaceutical composition as claimed in claim 9 wherein the carrier is silicon dioxide or hydroxypropylcellulose.

11. A pharmaceutical composition as claimed in claim 9 wherein the carrier is lactose.

12. A pharmaceutical composition as claimed in claim 11 in the form of a dry powder suitable for inhalation.

13. A pharmaceutical composition as claimed in claim 9 in the form of an aerosol spray presentation.

14. A pharmaceutical composition as claimed in claim 13 in which the aerosol spray presentation is a metered dose inhaler.

15. A pharmaceutical composition as claimed in claim 13 wherein the aerosol spray presentation comprises HFA134a as propellant.

16. A pharmaceutical composition as claimed in claim 9 comprising multicomponent particles comprising fluticasone propionate and carrier.

17. A method of treatment of a human or animal body suffering from a respiratory disorder, comprising administering to said human or animal body an effective amount of fluticasone propionate as claimed in claim 1.

18. A method of treatment as claimed in claim 17 wherein the respiratory disorder is asthma.

19. Fluticasone propionate as claimed in claim 1 which has a particle size in the range of 1 to 10 microns and a dynamic bulk density in the range between 0.05 and 0.179 g cm$^{-3}$.

20. Fluticasone propionate as claimed in claim 19 which has a uniformity coefficient of from 1 to 20.

21. Fluticasone propionate as claimed in claim 1 which has a respirable fraction of 14% or more by weight.

22. Fluticasone propionate as claimed in claim 5 which has a uniform coefficient of from 1 to 20 and a dynamic bulk density in the range between 0.05 and 0.17 g cm$^{-3}$.

23. A pharmaceutical composition comprising fluticasone propionate as claimed in claim 19 together with at least one pharmaceutically acceptable carrier excipient.

24. A pharmaceutical composition comprising fluticasone propionate as claimed in claim 20 together with at least one pharmaceutically acceptable carrier excipient.

25. A method of treatment of a human or animal body suffering from a respiratory disorder, comprising and administering to said human or animal body an effective amount of fluticasone propionate as claimed in claims 19.

26. A method of treatment of a human or animal body suffering from a respiratory disorder, comprising and administering to said human or animal body an effective amount of fluticasone propionate as claimed in claim 20.

27. A method of treatment of a human or animal body suffering from a respiratory disorder, comprising and administering to said human or animal body an effective amount of fluticasone propionate as claimed in claim 21.

28. A method of treatment of a human or animal body suffering from a respiratory disorder, comprising and administering to said human or animal body an effective amount of fluticasone propionate as claimed in claim 22.

* * * * *